(12) United States Patent
Ueda et al.

(10) Patent No.: US 6,518,436 B2
(45) Date of Patent: Feb. 11, 2003

(54) PROCESS FOR PREPARING PHARMACOLOGICALLY ACCEPTABLE SALT OF N-(1(S)-ETHOXYCARBONYL-3-PHENYLPROPYL)-L-ALANYL-AMINO ACID

(75) Inventors: Yasuyoshi Ueda, Himeji (JP); Koichi Kinoshita, Kakogawa (JP); Tadashi Moroshima, Kakogawa (JP); Yoshifumi Yanagida, Kakogawa (JP); Yoshihide Fuse, Himeji (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/989,186

(22) Filed: Nov. 21, 2001

(65) Prior Publication Data

US 2002/0087007 A1 Jul. 4, 2002

Related U.S. Application Data

(62) Division of application No. 09/269,107, filed as application No. PCT/JP98/03240 on Jul. 21, 1998, now Pat. No. 6,335,453.

(30) Foreign Application Priority Data

Jul. 22, 1997 (JP) .............................. 9-195865

(51) Int. Cl.$^7$ ........................................... C07D 207/04
(52) U.S. Cl. ..................................................... 548/533
(58) Field of Search ........................................... 548/533

(56) References Cited

U.S. PATENT DOCUMENTS

| 4,374,829 A | | 2/1983 | Harris et al. | |
| 6,335,453 B1 | * | 1/2002 | Ueda et al. | ................. 548/533 |

OTHER PUBLICATIONS

Abstract of Leo Gu, et al.; "Diketopiperazine formation, hydrolysis, and epimerization of the new dipeptide angiotensin–converting enzyme inhibitor RS–10085"; *Pharm Res.*(1987), 4(5), 392–397;Chemical Abstract Service; Database Accession No. 108:62328CA (abstract only).

Abstract of Katsumi Itoh, et al.; "Synthesis of compounds related to delapril (CV–3317)"; Takeda Kenkyushoho (1986), 45(3/4), 122–135; Chemical Abstract Service; Database Accession No. 107:154304CA.

J. Org. Chem. 1988, vol. 53, No. 4, pp. 836–844.

* cited by examiner

Primary Examiner—Joseph K. McKane
Assistant Examiner—Golam M M Shameem
(74) Attorney, Agent, or Firm—Armstrong, Westerman & Hattori, LLP

(57) ABSTRACT

There is provided a process for preparing a pharmacologically acceptable salt of N-(1(S)-ethoxycarbonyl-3-phenylpropyl)-L-alanyl-amino acid which comprises condensing an amino acid and N-(1(S) -ethoxycarbonyl-3-phenylpropyl)-L-alanine N-carboxy-anhydride under basic condition, carrying out decarboxylation under between neutral and acidic condition to obtain N-(1(S)-ethoxycarbonyl-3-phenylpropyl)-L-alanyl-amino acid, and forming a pharmacologically acceptable salt thereof, wherein the production of a by-product (3):

(3)

[Chemical structure: phenyl-$CH_2CH_2CH$-N with $COOCH_2CH_3$ substituent, connected to a ring containing $CH-CO$ with $CH_3$ substituent, $N-R^1$, and $CO-CH$ with $R^2$ substituent]

is suppressed by carrying out in an aqueous liquid a series of operations till formation of the pharmacologically acceptable salt or till isolation of the pharmacologically acceptable salt. The present invention enables to prepare the pharmacologically acceptable salt of N-(1(S)-ethoxycarbonyl-3-phenylpropyl)-L-alanyl-amino acid having high quality, in a commercial scale with high yield and economical efficiency.

8 Claims, No Drawings

PROCESS FOR PREPARING PHARMACOLOGICALLY ACCEPTABLE SALT OF N-(1(S)-ETHOXYCARBONYL-3-PHENYLPROPYL)-L-ALANYL-AMINO ACID

This application is a divisional of Ser. No. 09/269,107 filed Mar. 19, 1999, now U.S. Pat. No. 6,335,453, which was a 371 national phase of PCT/JP98/03240 filed Jul. 21, 1998.

TECHNICAL FIELD

The present invention relates to a process for economically preparing N-(1(S)-ethoxycarbonyl-3-phenylpropyl)-L-alanyl-amino acid represented by a formula (2):

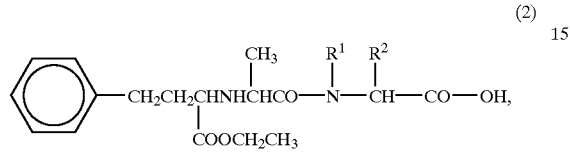
(2)

wherein a group:

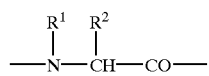

is, for example, a group represented by a formula:

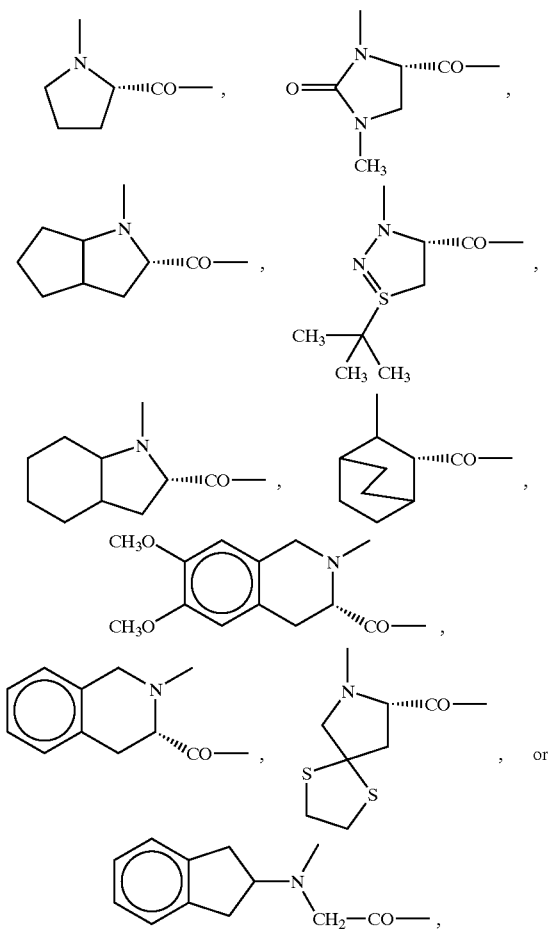

or a pharmacologically acceptable salt thereof having high quality, in high yield advantageously in a commercial scale.

The N-(1(S)-ethoxycarbonyl-3-phenylpropyl)-L-alanyl-amino acid (2) and the pharmacologically acceptable salt thereof are very useful compounds as various antihypertensive agents, such as N-(1(S)-ethoxycarbonyl-3-phenylpropyl)-L-alanyl-L-proline (enalapril) and its maleate (enalapril maleate).

BACKGROUND ART

As a method for obtaining the N-(1(S)-ethoxycarbonyl-3-phenylpropyl)-L-alanyl-amino acid (2) or the pharmacologically acceptable salt thereof, there has been known a method wherein an N-(1(S)-ethoxycarbonyl-3-phenylpropyl)-L-alanyl-amino acid (2) is produced starting from an amino acid represented by a formula (1):

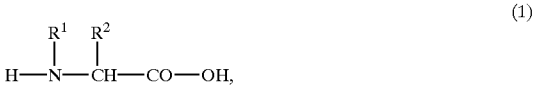
(1)

wherein a group:

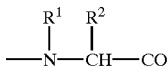

is the same as defined above, and N-(1(S)-ethoxycarbonyl-3-phenylpropyl)-L-alanine N-carboxyanhydride represented by a formula (8):

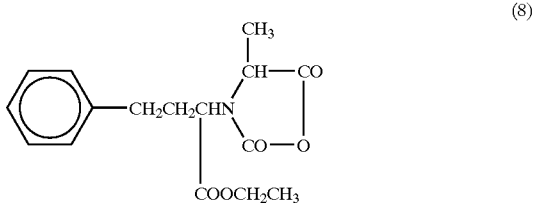
(8)

and then a pharmacologically acceptable salt thereof is formed therefrom. For example, there has been known a method for preparing N-(1(S)-ethoxycarbonyl-3-phenylpropyl)-L-alanyl-L-proline or its maleate as described in Japanese Unexamined Patent Publication No. 48696/1987.

The above-mentioned Japanese Unexamined Patent Publication No. 48696/1987 describes a method shown below.

1. N-(1(S)-Ethoxycarbonyl-3-phenylpropyl)-L-alanine. N-carboxyanhydride and 1 to 1.5 time molar amount of L-proline are condensed in a mixed solvent system of water and an organic solvent having high or low miscibility with water under basic condition (preferably pH 9 to 10) and, then, the condensation product is decarboxylated to obtain a reaction mixture containing N-(1(S)-ethoxycarbonyl-3-phenylpropyl)-L-alanyl-L-proline. The above-mentioned patent publication describes that high reaction yield is obtained in a mixed solvent system of water and an organic solvent having a high miscibility with water such as acetone.

2. The organic solvent having a high miscibility with water such as acetone is distilled away from the above-mentioned reaction mixture, and replaced with ethyl acetate which is an organic solvent having a low miscibility with water, and N-(1(S)-ethoxycarbonyl-3-phenylpropyl)-L-alanyl-L-proline is extracted therewith. In this procedure, the aqueous layer is saturated with sodium chloride to enhance the extraction efficiency of N-(1(S)-ethoxycarbonyl-3-phenylpropyl)-L-alanyl-L-proline having high water-solubility.

3. The extraction solution is dehydrated using anhydrous sodium sulfate and, then, the solvent is removed by concentration to obtain N-(1(S)-ethoxycarbonyl-3-phenylpropyl)-L-alanyl-L-proline.

4. N-(1(S)-Ethoxycarbonyl-3-phenylpropyl)-L-alanyl-L-proline and acetonitrile are mixed and to this mixture is added maleic acid with heating at 70° C. and the mixture is gradually cooled to obtain N-(1(S)-ethoxycarbonyl-3-phenylpropyl)-L-alanyl-L-proline maleate.

5. N-(1(S)-Ethoxycarbonyl-3-phenylpropyl)-L-alanyl-L-proline maleate is purified by recrystallization from acetonitrile.

However, it was found that methods in which N-(1(S)-ethoxycarbonyl-3-phenylpropyl)-L-alanyl-amino acid (2) is produced from an amino acid (1) and N-(1(S)-ethoxycarbonyl-3-phenylpropyl)-L-alanine N-carboxyanhydride, and then converted to a pharmacologically acceptable salt thereof, including the method described in the above-mentioned publication, potentially include problems of production of by-products, which causes disadvantages in yield and quality, a diketopiperazine derivative represented by a formula (3):

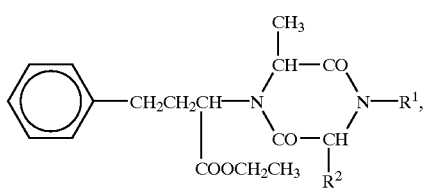

(3)

wherein a group:

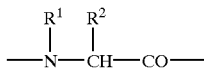

is the same as defined above, an N-(1(S)-carboxy-3-phenylpropyl)-L-alanyl-amino acid (hereinafter, also referred to as "carboxy derivative (4)") represented by a formula (4):

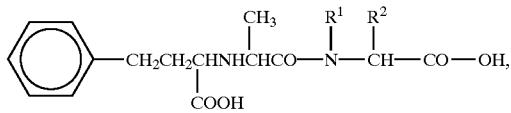

(4)

wherein a group:

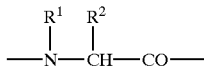

is the same as defined above, and N-(1(S)-ethoxycarbonyl-3-phenylpropyl)-L-alanine represented by a formula (5):

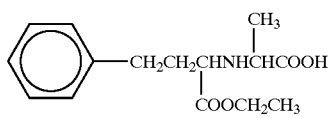

(5)

In particular, in the production in a commercial scale requiring longer operation time, production of a by-product diketopiperazine derivative (3) becomes remarkable, leading to unexpected reduction in the yield of a desired compound. Furthermore, when by-products, a carboxy derivative (4) and N-(1(S)-ethoxycarbonyl-3-phenylpropyl)-L-alanine (5), are produced, the removal of these compounds is extremely difficult and causes load in purification.

Moreover, the method described in Japanese Unexamined Patent Publication No. 48696/1987 has problems of complicated processes such as use of a large amount of an extraction solvent, use of various kinds of solvents, replacement of a reaction solvent with an extraction solvent and saturation of an aqueous layer with an inorganic salt, and problems of consumption of longer time, enlargement of the apparatus, increase in cost, and the like, due to such complicated processes.

As described above, it is very important to develop a simple method for economically preparing N-(1(S)-ethoxycarbonyl-3-phenylpropyl)-L-alanyl-amino acid (2) or a pharmacologically acceptable salt thereof having high quality with high yield in a commercial scale.

An object of the present invention is to provide an extremely simple method for economically preparing an N-(1((S)-ethoxycarbonyl-3-phenylpropyl)-L-alanyl-amino acid (2) and a pharmacologically acceptable salt thereof having high quality with high yield in a commercial scale whereby the production of the by-products, diketopiperazine derivative (3), carboxy derivative (4) and N-(1(S)-ethoxycarbonyl-3-phenylpropyl)-L-alanine (5), is suppressed.

An object of the present invention is, in particular, to provide an extremely simple method for economically preparing N-(1(S)-ethoxycarbonyl-3-phenylpropyl)-L-alanyl-L-proline and its maleate having high quality with high yield in a commercial scale, which method solves the above-mentioned problems.

First, it has been found that the production of the by-product diketopiperazine derivative (3) can be suppressed by carrying out, in the presence of water, a series of operations for producing an N-(1(S)-ethoxycarbonyl-3-phenylpropyl)-L-alanyl-amino acid (2) from an amino acid (1) and N-(1(S)-ethoxycarbonyl-3-phenylpropyl)-L-alanine. N-carboxyanhydride and forming a pharmacologically acceptable salt thereof and by reason of the protection effect from cyclization reaction by solvation as a protic solvent in addition to the dehydration suppressing effect which water essentially possesses, and also by selecting the condition that the N-carbamic acid produced in the reaction system is maintained as a basic salt.

Further it has been found that an N-(1(S)-ethoxycarbonyl-3-phenylpropyl)-L-alanyl-amino acid (2) having a low content of a diketopiperazine derivative (3), a carboxy derivative (4) and N-(1(S)-ethoxycarbonyl-3-phenylpropyl)-L-alanine (5) can be obtained by carrying out, in the presence of water under specific reaction conditions, the production of the N-(1(S)-ethoxycarbonyl-3-phenylpropyl)-L-alanyl-amino acid (2) from an amino acid (1) and N-(1(S)-ethoxycarbonyl-3-phenylpropyl)-L-alanine. N-carboxyanhydride.

Further it has been found that an N-(1(S)-ethoxycarbonyl-3-phenylpropyl)-L-alanyl-amino acid (2) and a pharmacologically acceptable salt thereof having high quality can be prepared with high yield according to an extremely simple process by combining the above-mentioned two methods.

Furthermore, it has been found that N-(1(S)-ethoxycarbonyl-3-phenylpropyl)-L-alanyl-L-proline can be separated extremely simply and efficiently, without saturation of an aqueous phase with an inorganic salt and without use of a large amount of extraction solvent, by carrying out extraction and separation operations under specific temperature condition, especially for the N-(1(S)-ethoxycarbonyl-3-phenylpropyl)-L-alanyl-L-proline having high water-solubility which requires complicated extraction and separation operations.

DISCLOSURE OF THE INVENTION

The present invention relates to (1) a process for preparing a pharmacologically acceptable salt of N-(1(S)-ethoxycarbonyl-3-phenylpropyl)-L-alanyl-amino acid represented by a formula (2):

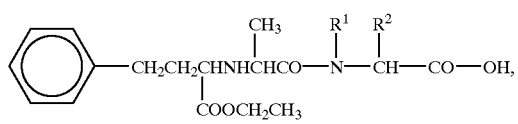

wherein a group:

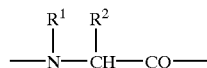

is a group selected from the group consisting of

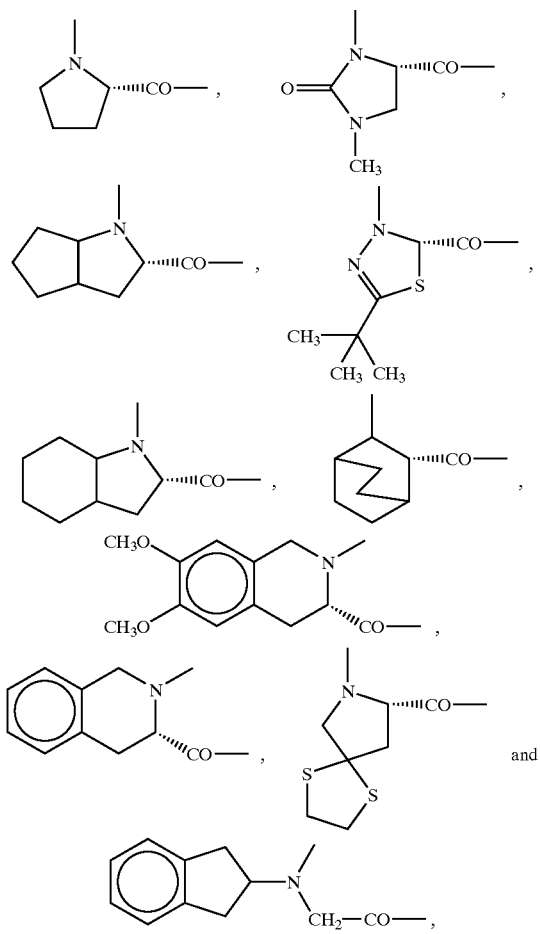

which comprises condensing an amino acid represented by a formula (1):

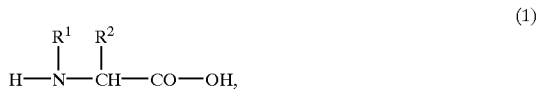

wherein a group:

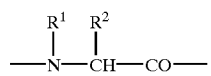

is the same as defined above, and N-(1(S)-ethoxycarbonyl-3-phenylpropyl)-L-alanine N-carboxyanhydride represented by a formula (8):

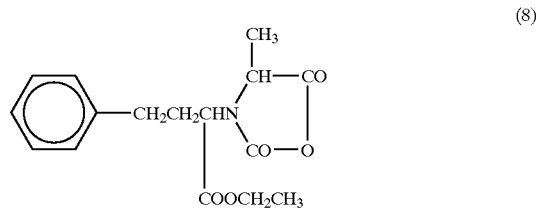

under basic condition, decarboxylating a produced carbamic acid derivative under between neutral and acidic condition to obtain an N-(1(S)-ethoxycarbonyl-3-phenylpropyl)-L-alanyl-amino acid (2), and forming a pharmacologically acceptable salt thereof, wherein the production of a by-product diketopiperazine derivative represented by a formula (3):

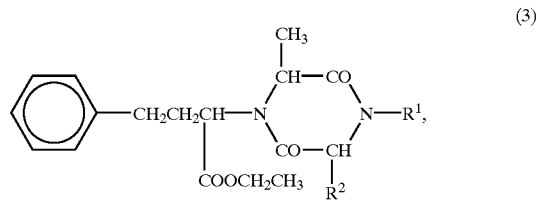

wherein a group:

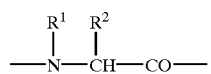

is the same as defined above, is suppressed by carrying out in an aqueous liquid a series of operations from the reaction to formation of the pharmacologically acceptable salt or a series of operations from the reaction to isolation of the pharmacologically acceptable salt, (2) the process of the above (1) wherein, in the reaction of producing the N-(1(S)-ethoxycarbonyl-3-phenylpropyl)-L-alanyl-amino acid (2), the condensation is carried out by gradually adding at least one of N-(1(S)-ethoxycarbonyl-3-phenylpropyl)-L-alanine. N-carboxyanhydride and a basic pH adjusting agent to an aqueous liquid containing the amino acid (1) and, if necessary, N-(1(S)-ethoxycarbonyl-3-phenylpropyl)-L-alanine. N-carboxyanhydride with the pH of the aqueous liquid maintained within a range of from 9 to 12, and then decarboxylation is carried out to obtain the N-(1(S)-ethoxycarbonyl-3-phenylpropyl)-L-alanyl-amino acid (2) having a low content of a diketopiperazine derivative represented by a formula (3):

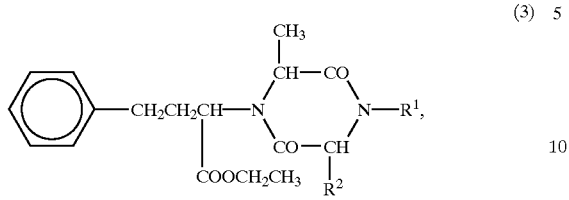

wherein a group:

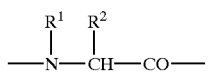

is the same as defined above, an N-(1(S)-carboxy-3-phenylpropyl)-L-alanyl-amino acid represented by a formula (4):

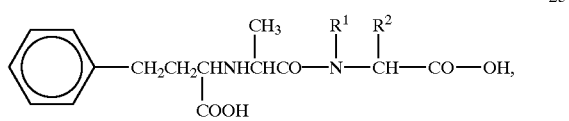

wherein a group:

is the same as defined above, and N-(1(S)-ethoxycarbonyl-3-phenylpropyl)-L-alanine represented by a formula (5):

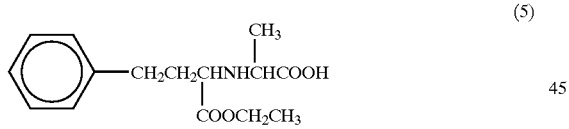

(3) the process of the above (2) wherein at least one of the N-(1(S)-ethoxycarbonyl-3-phenylpropyl)-L-alanine N-carboxyanhydride and basic pH adjusting agent is gradually added over at least ¼ hour, (4) the process of the above (1), (2) or (3) wherein at least 2 molar equivalents of the amino acid (1) is used based on N-(1(S)-ethoxycarbonyl-3-phenylpropyl)-L-alanine N-carboxyanhydride, (5) the process of the above (1) wherein, in the reaction of producing the N-(1(S)-ethoxycarbonyl-3-phenylpropyl)-L-alanyl-amino acid (2), the reaction is started by adding N-(1(S)-ethoxycarbonyl-3-phenylpropyl)-L-alanine N-carboxyanhydride to an aqueous liquid containing at least 2 molar equivalents of the amino acid (1) constituting a basic salt based on N-(1(S)-ethoxycarbonyl-3-phenylpropyl)-L-alanine. N-carboxyanhydride, and after the pH of the aqueous liquid reaches a range of from 9 to 12 a basic pH adjusting agent is gradually added to the aqueous liquid to carry out the condensation with the pH maintained within a range of from 9 to 12, and then decarboxylation is carried out to obtain the N-(1(S)-ethoxycarbonyl-3-phenylpropyl)-L-alanyl-amino acid (2) having a low content of a diketopiperazine derivative represented by a formula (3):

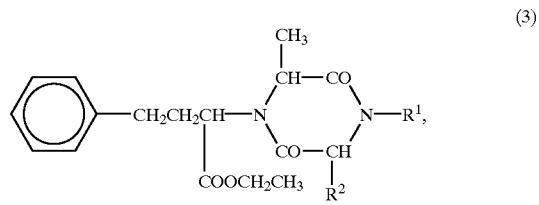

wherein a group:

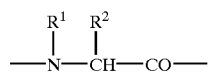

is the same as defined above, an N-(1(S)-carboxy-3-phenylpropyl)-L-alanyl-amino acid represented by a formula (4):

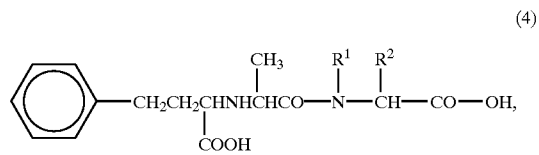

wherein a group:

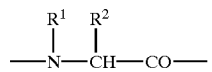

is the same as defined above, and N-(1(S)-ethoxycarbonyl-3-phenylpropyl)-L-anine represented by a formula (5):

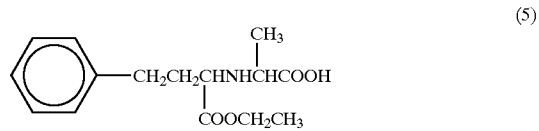

(6) the process of the above (2) or (5) wherein the pH of the aqueous liquid having a pH of from 9 to 12 is maintained within a range of pH 10.5±1.0, (7) the process of the above (1), (2), (3), (4), (5) or (6) wherein the aqueous liquid comprises an organic solvent and water in a weight ratio of from 96:4 to 0:100, (8) the process of the above (7) wherein the organic solvent is an organic solvent having a low miscibility with water, (9) the process of the above (7) or (8) wherein the organic solvent is at least one member selected from the group consisting of a halogenated hydrocarbon, a fatty acid ester, a ketone and an ether,

(10) the process of the above (2), (3), (4), (5), (6), (7), (8) or (9) wherein, in the condensation reaction of the amino acid (1) and N-(1(S)-ethoxycarbonyl-3- phenylpropyl)-L-alanine-N-carboxyanhydride, stirring and mixing are carried out at an agitating power of at least 0.1 kW/m³,

(11) the process of any one of the above (1) to (10) wherein the pharmacologically acceptable salt of the N-(1(S)-ethoxycarbonyl-3-phenylpropyl)-L-alanyl-amino acid (2) is formed in a medium comprising an organic solvent and water in a weight ratio of from 96:4 to 0:100 which medium contains the N-(1(S)-ethoxycarbonyl-3-phenylpropyl)-L-alanyl-amino acid (2), said N-(1(S)-ethoxycarbonyl-3-phenylpropyl)-L-alanyl-amino acid (2) being separated from a reaction mixture after the reaction by transferring the N-(1(S)-ethoxycarbonyl-3-phenylpropyl)-L-alanyl-amino acid (2) into either one phase in a two-phase medium comprising water and an organic solvent having a low miscibility with water,

(12) the process of the above (1), (2), (3), (4), (5), (6) or (7) wherein, in the operations of producing the N-(1(S)-ethoxycarbonyl-3-phenylpropyl)-L-alanyl-amino acid (2) and forming the pharmacologically acceptable salt thereof, the series of operations from the reaction to formation of the pharmacologically acceptable salt or the series of operations from the reaction to isolation of the pharmacologically acceptable salt is carried out in an aqueous liquid essentially consisting of water,

(13) the process of any one of the above (1) to (12) wherein the amino acid (1) is L-proline and the produced N-(1(S)-ethoxycarbonyl-3-phenylpropyl)-L-alanyl-amino acid (2) is N-(1(S)-ethoxycarbonyl-3-phenylpropyl)-L-alanyl-L-proline,

(14) the process of the above (13) wherein using a two-phase liquid comprising water and an organic solvent having a low miscibility with water, N-(1(S)-ethoxycarbonyl-3-phenylpropyl)-L-alanyl-L-proline is transferred into the organic solvent phase by separating the two-phase liquid at temperature of at least 20° C. or is transferred into the water phase by separating the two-phase liquid at a temperature of less than 20° C., and the pharmacologically acceptable salt thereof is formed in the organic solvent phase or the water phase and, if necessary, isolated,

(15) the process of the above (13) or (14) wherein the pharmacologically acceptable salt thereof is maleic acid salt thereof,

(16) the process of the above (15) wherein steps for forming and crystallizing the salt are carried out in an aqueous liquid essentially consisting of water in which an inorganic salt coexists,

(17) the process of the above (13), (14), (15) or (16) wherein the maleic acid salt thereof is formed by gradually adding an aqueous liquid containing N-(1(S)-ethoxycarbonyl-3-phenylpropyl)-L-alanyl-L-proline to an aqueous liquid containing maleic acid,

(18) the process of the above (15), (16) or (17) wherein the steps for forming and crystallizing the salt are carried out at from 40 to 70° C.

(19) the process of any one of the above (1) to (18) wherein at least an equimolar amount of water exists based on a produced N-(1(S)-ethoxycarbonyl-3-phenylpropyl)-L-alanyl-amino acid (2), in the series of operations from the reaction of producing the N-(1(S)-ethoxycarbonyl-3-phenylpropyl)-L-alanyl-amino acid (2) to formation of the pharmacologically acceptable salt or the series of operations from the reaction to isolation of the pharmacologically acceptable salt,

(20) a process for preparing N-(1(S)-ethoxycarbonyl-3-phenylpropyl)-L-alanyl-L-proline maleate wherein a process in which steps for forming and crystallizing a salt in an aqueous liquid containing N-(1(S)-ethoxycarbonyl-3-phenylpropyl)-L-alanyl-L-proline and maleic acid are carried out in an aqueous liquid essentially consisting of water, is carried out in the coexistence of an inorganic salt and/or at from 40 to 70° C.,

(21) the process of the above (20) wherein the process is carried out using a reaction mixture after production of N-(1(S)-ethoxycarbonyl-3-phenylpropyl)-L-alanyl-L-proline,

(22) a process for preparing a pharmacologically acceptable salt of N-(1((S)-ethoxycarbonyl-3-phenylpropyl)-L-alanyl-amino acid represented by a formula (2):

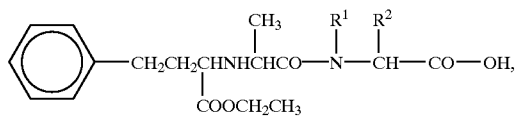

wherein a group:

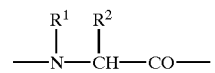

is a group selected from the group consisting of

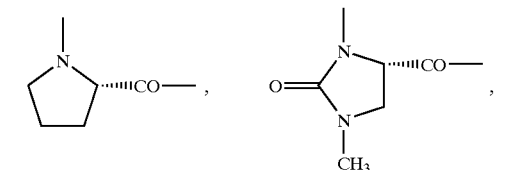

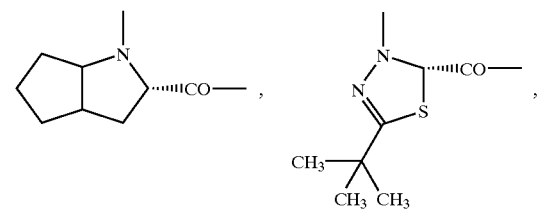

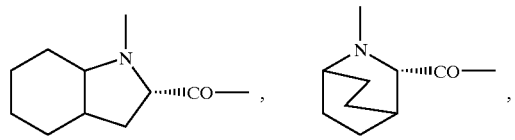

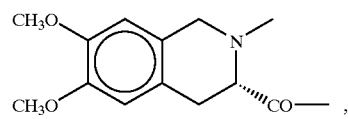

-continued

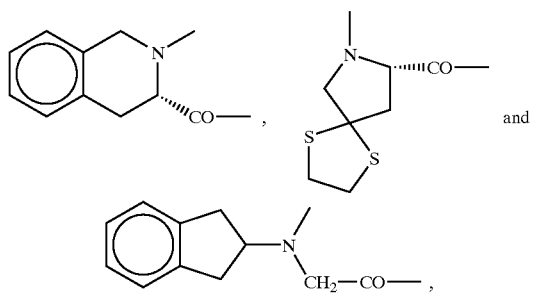

which comprises forming a pharmacologically acceptable salt of N-(1(S)-ethoxycarbonyl-3-phenylpropyl)-L-alanyl-amino acid from an N-(1(S)-ethoxycarbonyl-3-phenylpropyl)-L-alanyl-amino acid (2) contained in a reaction mixture after production of the N-(1(S)-ethoxycarbonyl-3-phenylpropyl)-L-alanyl-amino acid (2) and, if necessary, isolating the pharmacologically acceptable salt, wherein the production of a by-product diketopiperazine derivative represented by a formula (3):

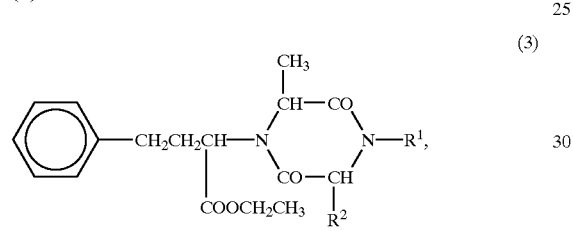

wherein a group:

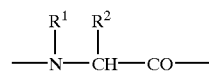

is the same as defined above, is suppressed by carrying out an operation in a medium comprising an organic solvent and water in which the proportion of water is higher than a weight ratio of the organic solvent/water of 96/4,

(23) the process of the above (22) wherein the pharmacologically acceptable salt is formed in the organic solvent phase in which water coexists and which is obtained by extracting or washing the reaction mixture containing the N-(1(S)-ethoxycarbonyl-3-phenylpropyl)-L-alanyl-amino acid (2) and, if necessary, the pharmacologically acceptable salt thereof is isolated,

(24) the process of the above (22) or (23) wherein at least an equimolar amount of water exists based on the N-(1(S)-ethoxycarbonyl-3-phenylpropyl)-L-alanyl-amino acid (2) in the operations of forming and, if necessary, isolating the pharmacologically acceptable salt of N-(1(S)-ethoxycarbonyl-3-phenylpropyl)-L-alanyl-amino acid (2),

(25) the process of the above (22), (23) or (24) wherein the N-(1(S)-ethoxycarbonyl-3-phenylpropyl)-L-alanyl-amino acid (2) is N-(1(S)-ethoxycarbonyl-3-phenylpropyl)-L-alanyl-L-proline,

(26) the process of the above (22), (23), (24) or (25) wherein the pharmacologically acceptable salt is a maleic acid salt,

(27) the process of the above (22), (23), (24), (25) or (26) wherein steps for forming and crystallizing the salt are carried out at from 40 to 70° C.,

(28) a process for separating N-(1(S)-ethoxycarbonyl-3-phenylpropyl)-L-alanyl-L-proline wherein, by separating a two-phase medium comprising water and an organic solvent having a low miscibility with water which medium contains N-(1(S)-ethoxycarbonyl-3-phenylpropyl)-L-alanyl-L-proline, at a temperature of at least 20° C., N-(1(S)-ethoxycarbonyl-3-phenylpropyl)-L-alanyl-L-proline is transferred into the organic solvent phase or, by separating the two-phase medium at a temperature of less than 20° C., N-(1(S)-ethoxycarbonyl-3-phenylpropyl)-L-alanyl-L-proline is transferred into the water phase,

(29) the process of the above (28) wherein the organic solvent is an acetic acid ester,

(30) the process of the above (28) or (29) wherein, in the process for transferring N-(1(S)-ethoxycarbonyl-3-phenylpropyl)-L-alanyl-L-proline into the organic solvent phase, the transfer is carried out without saturating the water phase with an inorganic salt,

(31) a process for preparing N-(1(S)-ethoxycarbonyl-3-phenylpropyl)-L-alanyl-L-proline which comprises producing N-(1(S)-ethoxycarbonyl-3-phenylpropyl)-L-alanyl-L-proline from L-proline and N-(1(S)-ethoxycarbonyl-3-phenylpropyl)-L-alanine. N-carboxyanhydride, wherein condensation is carried out by gradually adding at least one of N-(1(S)-ethoxycarbonyl-3-phenylpropyl)-L-alanine. N-carboxyanhydride and a basic pH adjusting agent to an aqueous liquid containing L-proline and, if necessary, N-(1(S)-ethoxycarbonyl-3-phenylpropyl)-L-alanine. N-carboxyanhydride, with the pH of the aqueous liquid maintained within a range of from 9 to 12, and then decarboxylation is carried out under between neutral and acidic condition to obtain N-(1(S)-ethoxycarbonyl-3-phenylpropyl)-L-alanyl-L-proline having a low content of a diketopiperazine derivative represented by a formula (6):

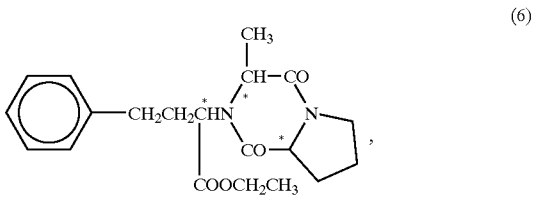

wherein all asymmetric carbon atoms with * have (S)-configuration, N-(1(S)-carboxy-3-phenylpropyl)-L-alanyl-L-proline represented by a formula (7):

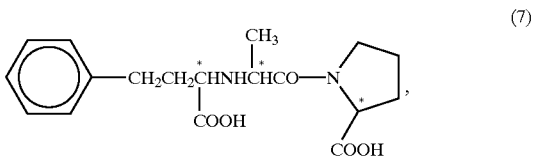

wherein all asymmertric carbon atoms with * have (S)-configuration, and N-(1(S)-ethoxycarbonyl-3-phenylpropyl)-L-alanine represented by a formula (5):

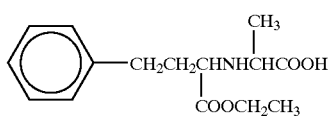

(5)

(32) the process of the above (31) wherein at least one of the N-(1(S)-ethoxycarbonyl-3-phenylpropyl)-L-alanine. N-carboxyanhydride and the basic pH adjusting agent is added over at least ¼ hour,

(33) the process of the above (31) or (32) wherein at least 2 molar equivalents of L-proline is used based on N-(1(S)-ethoxycarbonyl-3-phenylpropyl)-L-alanine. N-carboxyanhydride,

(34) a process for preparing N-(1(S)-ethoxycarbonyl-3-phenylpropyl)-L-alanyl-L-proline which comprises producing N-(1(S)-ethoxycarbonyl-3-phenylpropyl)-L-alanyl-L-proline from L-proline and N-(1(S)-ethoxycarbonyl-3-phenylpropyl)-L-alanine. N-carboxyanhydride, wherein a reaction is started by adding N-(1(S)-ethoxycarbonyl-3-phenylpropyl)-L-alanine N-carboxyanhydride to an aqueous liquid containing at least 2 molar equivalents of L-proline constituting a basic salt based on N-(1(S)-ethoxycarbonyl-3-phenylpropyl)-L-alanine. N-carboxyanhydride, and after the pH of the aqueous liquid reaches a range of from 9 to 12 a basic pH adjusting agent is gradually added to the aqueous liquid to carry out a condensation with the pH maintained within a range of from 9 to 12, and then decarboxylation is carried out under between neutral and acidic condition to obtain N-(1(S)-ethoxycarbonyl-3-phenylpropyl)-L-alanyl-L-proline having a low content of a diketopiperazine derivative represented by a formula (6):

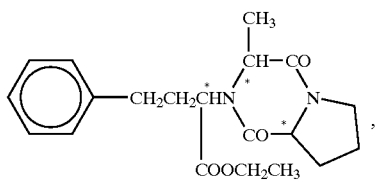

(6)

wherein all asymmetric carbon atoms with * have (S)-configuration, N-(1(S)-carboxy-3-phenylpropyl)-L-alanyl-L-proline represented by a formula (7):

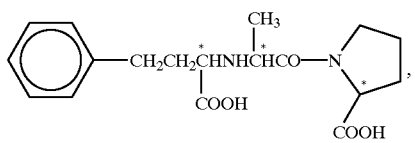

(7)

wherein all asymmertric carbon atoms with * have (S)-configuration, and N-(1(S)-ethoxycarbonyl-3-phenylpropyl)-L-alanine represented by a formula (5):

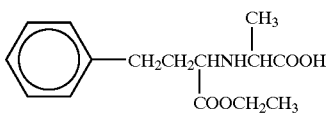

(5)

(35) the process of the above (31), (32), (33) or (34) wherein the aqueous liquid comprises an organic solvent and water in a weight ratio of from 96:4 to 0:100,

(36) the process of the above (31), (32), (33), (34) or (35) wherein, in the reaction of L-proline and N-(1(S)-ethoxycarbonyl-3-phenylpropyl)-L-alanine N-carboxyanhydride, stirring and mixing are carried out at an agitating power of at least 0.1 kW/m$^3$,

(37) the process of the above (35) or (36) wherein the organic solvent is at least one member selected from the group consisting of a halogenated hydrocarbon, a fatty acid ester, a ketone and an ether,

(38) the process of the above (31), (32), (33), (34), (35) or (36) wherein the reaction of producing N-(1(S)-ethoxycarbonyl-3-phenylpropyl)-L-alanyl-L-proline is carried out in an aqueous liquid essentially consisting of water,

(39) a process for purifying a pharmacologically acceptable salt of N-(1(S)-ethoxycarbonyl-3-phenylpropyl)-L-alanyl-amino acid represented by a formula (2):

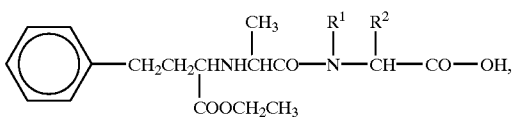

(2)

, wherein a group:

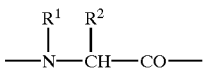

is a group selected from the group consisting of

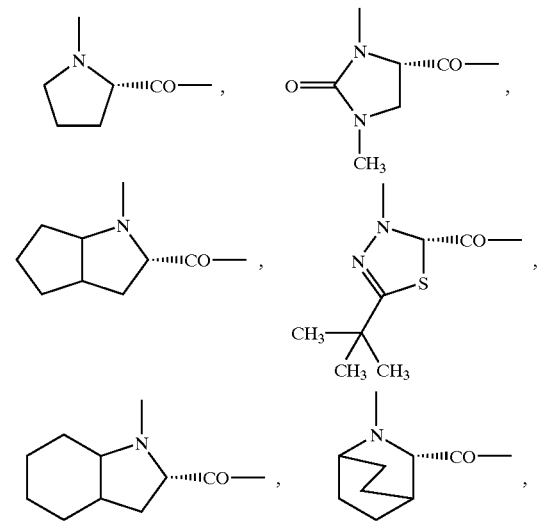

-continued

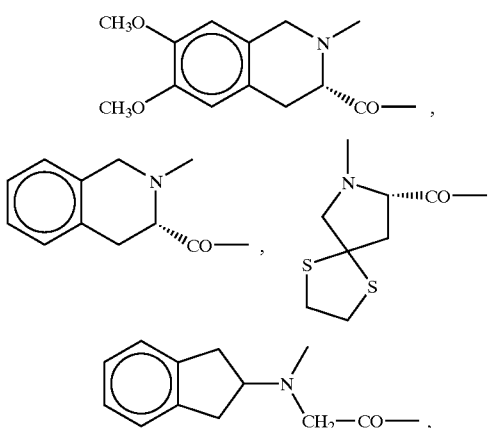

wherein the purification is carried out in an aqueous liquid whereby the production of a by-product diketopiperazine derivative represented by a formula (3):

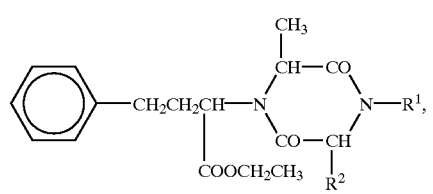

wherein a group:

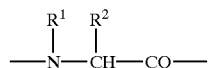

is the same as defined above, is suppressed and also the N-(1(S)-ethoxycarbonyl-3-phenylpropyl)-L-alanyl-amino acid (2) and pharmacologically acceptable salt thereof having a low content of an N-(1(S)-carboxy-3-phenylpropyl)-L-alanyl-amino acid represented by a formula (4):

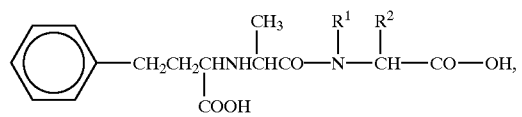

wherein a group:

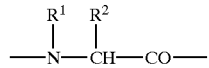

is the same as defined above, and N-(1(S)-ethoxycarbonyl-3-phenylpropyl)-L-alanine represented by a formula (5):

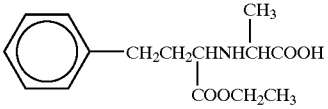

is obtained,

(40) the process of the above (39) wherein the aqueous liquid is a medium comprising an organic solvent and water in which the proportion of water is higher than a weight ratio of the organic solvent/water of 96/4,

(41) the process of the above (39) or (40) wherein the purification of the pharmacologically acceptable salt is carried out at from 40 to 70° C.

(42) a process for purifying N-(1(S)-ethoxycarbonyl-3-phenylpropyl)-L-alanyl-L-proline maleate which comprises carrying out the purification of N-(1(S)-ethoxycarbonyl-3-phenylpropyl)-L-alanyl-L-proline maleate in an aqueous liquid essentially consisting of water, wherein the maleate is purified in the coexistence of an inorganic salt and/or at from 40 to 70° C. whereby the production of a by-product diketopiperazine derivative represented by a formula (6):

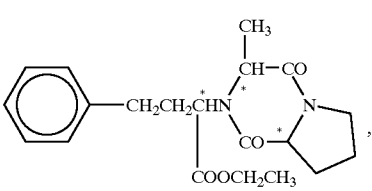

wherein all asymmetric carbon atoms with * have (S)-configuration, is suppressed and also N-(1(S)-ethoxycarbonyl-3-phenylpropyl)-L-alanyl-L-proline maleate having a low content of N-(1(S)-carboxy-3-phenylpropyl)-L-alanyl-L-proline represented by a formula (7):

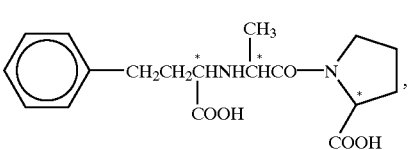

wherein all asymmertric carbon atoms with * have (S)-configuration, and N-(1(S)-ethoxycarbonyl-3-phenylpropyl)-L-alanine represented by a formula (5):

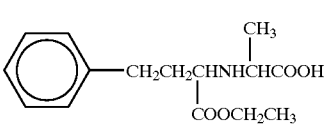

is obtained, and

(43) the process of the above (39), (40), (41) or (42) wherein the purification method is recrystallization or reslurry washing.

BEST MODE FOR CARRYING OUT THE INVENTION

The amino acid in the present invention represented by the formula (1):

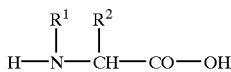 (1)

is an amino acid wherein the group:

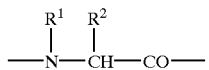

in the formula is a group selected from the group of an imino acid residue, preferably of a cyclic imino acid residue. In the case of an imino acid residue, $R^1$ is an alicyclic monocyclic or bicyclic series having 5 to 10 ring members and $R^2$ is hydrogen atom. Representative examples of the imino acid residue are, for example, a group represented by a formula:

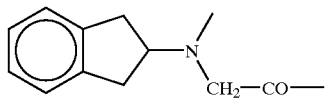

and the like.

In the case of a cyclic imino acid residue, $R^1$ and $R^2$ are combined and, together with nitrogen and carbon atoms to which $R^1$ and $R^2$ are connected, form a heterocyclic monocyclic or bicyclic series having 5 to 10 ring members. The above-mentioned cyclic imino acid residue is, for example, a residue of proline or proline analogue, or a group derived from them and, in the above-mentioned group, the pyrrolidine ring can be exchanged for, for example, piperidine ring, quinuclidine ring, isoindoline ring, N-alkylimidazolidine ring, octahydroindole ring, octahydroisoindole ring, decahydroquinoline ring, decahydroisoquinoline ring, 1,2,3,4-tetrahydroisoquinoline ring and similar ring thereto. These rings may be substituted or linked by an oxo group, hydroxyl group, mercapto group, an alkylmercapto group, an alkoxy group, an alkyl group or the like. Representative examples of the cyclic imino acid residue are groups represented by formulae:

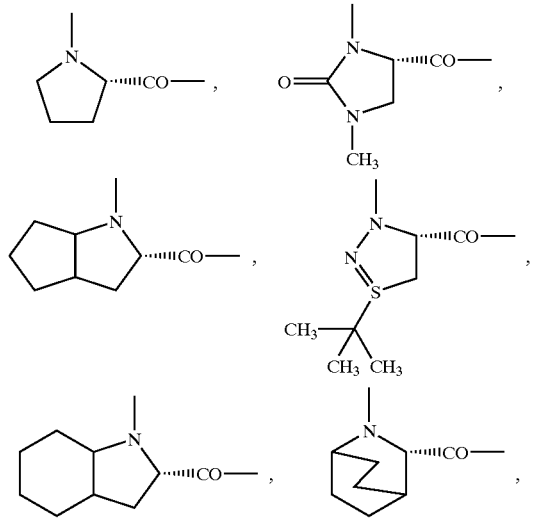

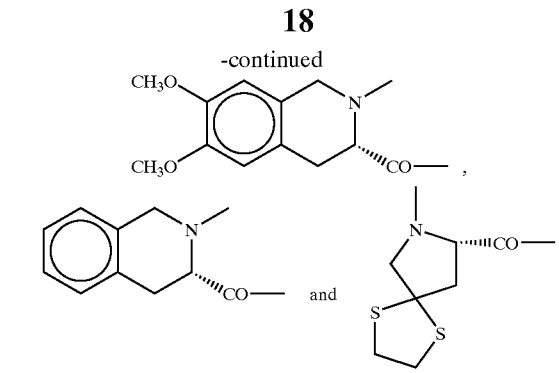

and the like.

Among these amino acids, for example, L-proline and 1,2,3,4-tetrahydro-3-isoquinolinecarboxylic acid are commercially available. 1,2,3,4-Tetrahydro-6,7-dimethoxy-3-isoquinolinecarboxylic acid is obtained by a method described in, for example, U.S. Pat. No. 4,912,221 and 1,4-dithia-7-azaspiro[4,4]nonane-8-carboxylic acid is obtained by a method described in, for example, U.S. Pat. No. 4,468,396. Further, 1-methyl-2-oxo-4-imidazolidine-carboxylic acid, octahydrocyclopenta[b]pyrrole-2-carboxylic acid and 2-azabicyclo[2,2,2]octane-3-carboxylic acid are obtained, for example, by methods described in Int. J. Pept. Protein Res., 33(6), 403–11(1989), Tetrahedron Lett., 34(41), 6603–6(1993) and Tetrahedron Lett., 33(48), 7369–72(1992), respectively.

The N-(1(S)-ethoxycarbonyl-3-phenylpropyl)-L-alanine. N-carboxyanhydride used in the present invention can be prepared according to methods described in, for example, Japanese Unexamined Patent Publication No. 48696/1987, U.S. Pat. Nos. 4,686,295 and 5,359,086, and the like. For example, the N-carboxyanhydride can be easily prepared approximately quantitatively by adding a phosgene solution or introducing a phosgene gas to N-(1(S)-ethoxycarbonyl-3-phenylpropyl)-L-alanine (5) or its inorganic acid salt such as a hydrochloride in an organic solvent and by reacting them with heating. The N-(1(S)-ethoxycarbonyl-3-phenylpropyl)-L-alanine. N-carboxyanhydride produced by the reaction can be usually used in the form of a reaction solution as obtained without particular purification after removal of the remaining phosgene and hydrogen chloride, or can also be crystallized for use. In the case of a reaction solution, it is advantageous to use an organic solvent having a low miscibility with water as a reaction solvent so that in the present invention it can be suitably used as it is. In the case of being crystallized for use, the subsequent present invention can be carried out without using an organic solvent at all.

In the N-(1(S)-ethoxycarbonyl-3-phenylpropyl)-L-alanyl-amino acid in the present invention represented by the formula (2):

(2)

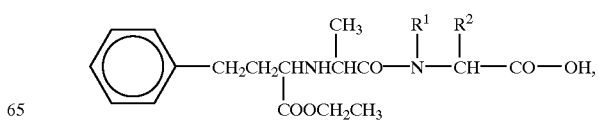

a group:

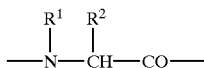

is the same as defined above. The above-mentioned imino acid residue and cyclic imino acid residue contribute to exhibiting of excellent antihypertensive action. When in the formula (2) the carbon atom to which a carboxyl group is connected is an asymmetric carbon atom, the compound (2) in which this carbon atom has (S)-configuration is generally useful as an antihypertensive agent. When another asymmetric carbon atom exists, one having desired configuration based on this asymmetric carbon atom can be used. In the case that the above-mentioned group:

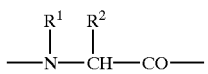

is a group represented by a formula:

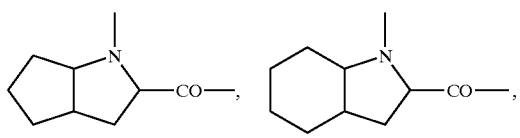

particularly desirable configuration thereof is, for example,

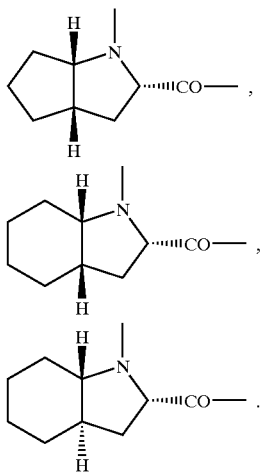

When the above-mentioned cyclic imino acid residue is a proline residue, particularly a L-form (namely, (S)-configuration) proline residue, the product (2) is enalapril, a particularly useful antihypertensive agent.

Examples of the pharmacologically acceptable salt of N-(1(S)-ethoxycarbonyl-3-phenylpropyl)-L-alanyl-amino acid (2) obtained by the present invention include an inorganic acid salt such as hydrochloride, sulfate or phosphate, an organic acid salt such as acetate, maleate, fumarate, tartarate or citrate, an amino acid adduct such as glycine or phenylalanine.

The aqueous liquid means a solution in which water coexists, and examples of the aqueous liquid include water or a mixture of an organic solvent and water. The above-mentioned organic solvent may be either an organic solvent having a high miscibility with water or an organic solvent having a low miscibility with water.

Examples of the organic solvent having a high miscibility with water include, for example, acetone, acetonitrile, tetrahydrofuran (THF), dioxane, a mixture thereof and the like. Among these, acetone and tetrahydrofuran are preferred from viewpoints of easy handling and safety of the solvent. This organic solvent having a high miscibility with water means a solvent that when mildly mixed with the same volume of pure water generally at 20° C. under one atmosphere, uniform appearance of the mixture remains even after the flow ceases.

Examples of the organic solvent having a low miscibility with water include, for example, a halogenated hydrocarbon such as methylene chloride, chloroform or 1,2-dichloroethane; a fatty acid ester such as methyl acetate, ethyl acetate, n-propyl acetate, isopropyl acetate, n-butyl acetate, isobutyl acetate, methyl propionate or ethyl propionate; a ketone such as methyl ethyl ketone, methyl n-propyl ketone, diethyl ketone or methyl isobutyl ketone; a hydrocarbon such as toluene or n-hexane; an ether such as diethyl ether, dipropyl ether, diisopropyl ether, dibutyl ether or methyl tert-butyl ether; a mixture thereof; and the like. Among these, a halogenated hydrocarbon, a fatty acid ester, a ketone and an ether are preferred from viewpoint of solubility for N-(1(S)-ethoxycarbonyl-3-phenylpropyl)-L-alanine. N-carboxyanhydride, and the like, and among them, a fatty acid ester, particularly an acetate, more particularly ethyl acetate, is preferred from viewpoints of easy handling, safety of the solvent, cost of the solvent, use advantage as a solvent in extraction and salt formation, high effect for stabilizing N-(1(S)-ethoxycarbonyl-3-phenylpropyl)-L-alanyl-amino acid (2) (effect for suppressing the production of a by-product diketopiperazine derivative (3)) and the like. This organic solvent having a low miscibility with water means an organic solvent other than the above-mentioned organic solvent having a high miscibility with water.

Further, the above-mentioned organic solvents can be used together. For example, the organic solvent having a high miscibility with water and the organic solvent having a low miscibility with water can be used together.

The ratio of the organic solvent to water in the above-mentioned aqueous liquid differs depending on solubilities of a reactant (1) and a product (2). The weight ratio is from 96:4 to 0:100, generally from 20:1 to 0:100 and is normally from 10:1 to 0:100 from viewpoint of productivity. When the amino acid (1) is L-proline and the product (2) is N-(1(S)-ethoxycarbonyl-3-phenylpropyl)-L-alanyl-L-proline (enalapril), the weight ratio of the organic solvent to water may also be from 96:4 to 0:100, and is preferably from 20:1 to 0:100, particularly from 10:1 to 0:100 from viewpoint of productivity. The aqueous liquid may be an aqueous liquid essentially consisting of water.

The "aqueous liquid essentially consisting of water" in the present invention means an aqueous system which may contain an organic solvent to an extent that in the reaction and salt formation, a resulting effect is nearly the same with an effect given when carrying out the reaction and salt formation in a water alone. A ratio of water contained therein varies depending on the kind of an organic solvent used and steps.

It is desirable that the amount of water is normally at least equivalent mole, preferably at least 2-fold mole, more preferably at least 3-fold mole, further preferably at least 4-fold mole, based on the product (2), since the production of a by-product diketopiperazine derivative (3) is suppressed. For example, the production of the by-product (3) can be suppressed to at most ½ to ⅓, preferably to almost negligible level as described in Examples 8 and 10 shown below.

In the process of the present invention, N-(1(S)-ethoxycarbonyl-3-phenylpropyl)-L-alanine. N-carboxyanhydride and an amino acid (1) are first condensed in an aqueous liquid under basic condition to obtain a carbamic acid derivative.

Examples of the basic pH adjusting agent used in the present invention for carrying out the condensation reaction under basic condition include, for example, an inorganic base such as a hydroxide, carbonate or hydrogencarbonate of alkaline metal or alkaline earth metal, and an organic base such as a secondary amine, tertiary amine or quaternary ammonium hydroxide. Concrete examples thereof include, for example, an alkaline metal hydroxide such as sodium hydroxide, potassium hydroxide or lithium hydroxide; an alkaline metal carbonate such as sodium carbonate, potassium carbonate or lithium carbonate; an alkaline metal hydrogencarbonate such as sodium hydrogencarbonate or potassium hydrogencarbonate; an alkaline earth metal hydroxide such as magnesium hydroxide or calcium hydroxide; a secondary amine such as dimethylamine, diethylamine, diisopropylamine or dicyclohexylamine; a tertiary amine such as triethylamine, tripropylamine, tributylamine, triamylamine, pyridine or N-methylmorpholine; a quaternary ammonium hydroxide such as tetramethyl-, tetraethyl-, tetrapropyl-, tetrabutyl-, tetraamyl-, tetrahexyl- or benzyltrimethyl-ammonium hydroxide. However, the basic pH adjusting agent is not limited to those examples.

As to the basic pH adjusting agent, an inorganic base, particularly an alkaline metal hydroxide such as sodium hydroxide, potassium hydroxide or lithium hydroxide is preferred and, further, sodium hydroxide and potassium hydroxide are preferred, from viewpoints of inexpensiveness, easy handling and easy disposal of waste water. The above-mentioned inorganic base is preferably used in the form of an aqueous solution thereof from viewpoint of operability, and normally, it is advantageous that the base is used, for example, in the form of a 2 to 20 N, preferably 5 to 20 N aqueous solution of an alkaline metal hydroxide. The above-mentioned basic pH adjusting agent may be used alone and may also be used in admixture of two or more thereof.

The amount used of the above-mentioned basic pH adjusting agent is an amount necessary for maintaining an aqueous liquid at specific basicity.

An aqueous liquid is adjusted to basic with the above-mentioned basic pH adjusting agent, however, there is no need to add a base separately for adjusting the aqueous liquid to basic. There can be used, as the aqueous liquid, an aqueous liquid which has been made to have a pH buffering action by adding disodium hydrogenphosphate, hydrochloric acid, boric acid or the like, and a surfactant, a phase-transfer catalyst etc. may also be added if necessary.

For securing a high yield and high quality consistently in the present reaction, it is important to suppress side reactions such as production of a carboxy derivative (4) and N-(1(S)-ethoxycarbonyl-3-phenylpropyl)-L-alanine (5) due to hydrolysis in reacting and to allow the main reaction to proceed smoothly. For this, it is beneficial to carry out the condensation at pH 9 to 12 with gradually adding at least one of N-(1(S)-ethoxycarbonyl-3-phenylpropyl)-L-alanine. N-carboxyanhydride and a basic pH adjusting agent to an aqueous liquid containing an amino acid (1) and, if necessary, N-(1(S)-ethoxycarbonyl-3-phenylpropyl)-L-alanine. N-carboxyanhydride. By this, it is possible to suppress the production of by-products to at most ½ to ⅓ as a whole and reduce the content of the by-products (3) to (5) in the product (2) to concretely less than 5% by weight, preferably less than 2% by weight, such as in Example 7 described below. Therefore, the yield of the desired product (2) can be raised to a level of 95% or more.

In this case, increase in the amount of the amino acid (1) used is also effective for smoothly proceeding the main reaction with suppressing a side-reaction such as hydrolysis. Specifically, use of at least 2 molar equivalents of an amino acid (1) based on N-(1(S)-ethoxycarbonyl-3-phenylpropyl)-L-alanine. N-carboxyanhydride is preferable since it further enhances the effect.

The time for addition of at least one of N-(1(S)-ethoxycarbonyl-3-phenylpropyl)-L-alanine. N-carboxyanhydride and a basic pH adjusting agent is, in terms of time for addition of whole amount, generally at least ¼ hour, normally at least ⅓ hour, preferably at least ½ hour, and there is no upper limit, however, it is generally at most 20 hours, normally at most 15 hours, preferably at most 10 hours, from viewpoint of productivity and the like. As the gradual addition method, there can be employed, for example, a method in which materials are added at constant rate, a method in which materials are added portionwise, and the like, and particularly, the method in which materials are added at constant rate is preferably employed from viewpoint of improvement in yield and quality, operability and the like. The N-(1(S)-ethoxycarbonyl-3-phenylpropyl)-L-alanine. N-carboxyanhydride can be added, for example, after mixing or dissolving in a solvent used in the above-mentioned reaction before addition, or can be added as it is in the form of a powder.

By this, generally the reaction can be suitably carried out not only in a mixed solvent system of water and an organic solvent having a high miscibility with water but also in a mixed solvent system of water and an organic solvent having a low miscibility with water. And in the reaction in an aqueous liquid essentially consisting of water in which the proportion of water in an aqueous liquid used is increased and the effect for suppressing the production of the diketopiperazine derivative (3) is maximized, there is a tendency that the reaction rate of main reaction decreases and the influence by side-reaction due to the elongation of reaction time increases. Therefore, it is suitable for solving the above-mentioned problems that the proportion constituting a basic salt as an active species of the amino acid (1) used is increased, and specifically, N-(1(S)-ethoxycarbonyl-3-phenylpropyl)-L-alanine. N-carboxyanhydride is added to an aqueous liquid in which said active species exists in an amount of at least 2 molar equivalents based on the N-(1 (S)-ethoxycarbonyl-3-phenylpropyl)-L-alanine N-carboxyanhydride for reaction. This condition also includes a case in which the pH of an aqueous liquid at the start of the reaction is over 12. However, when condensation reaction is effected with maintaining the pH within a range of from 9 to 12 by gradually adding a basic pH adjusting agent to a reaction liquid after the pH reaches the range from 9 to 12 as a result of steep reduction of the pH accompanying smooth proceeding of the main reaction, the N-carbamic group produced is maintained as its basic salt and the amount of the active species of the above-mentioned amino acid (1) is always maintained at maximum, and thereby the reaction time can be shortened and the production of the carboxy derivative (4) and N-(1(S)-ethoxycarbonyl-3-phenylpropyl)-L-alanine (5) owing to hydrolysis can be minimized. By this, the reaction can be carried out particularly suitably even in the case that reaction field is substantially water.

Advantageously the range of the pH maintained at 9 to 12 is preferably within the range of pH 10.5±1.0, more preferably within the range of pH 10.5±0.5.

When the pH in reaction is out of the above-mentioned range, the total amount of the by-products tends to increase. When the pH is lower, the main reaction does not easily proceed, and N-(1(S)-ethoxycarbonyl-3-phenylpropyl)-L-alanine (5) tends to be produced due to hydrolysis of the carboxyanhydride moiety. On the other hand, when the pH is higher, a carboxy derivative (4) tends to be produced due to hydrolysis of the ethoxycarbonyl moiety.

Regarding the reaction, since there is a tendency that the reaction system becomes heterogeneous system of liquid-liquid or solid-liquid particularly in a mixed solvent system of water and an organic solvent having a low miscibility with water or in an aqueous liquid essentially consisting of water, it is preferable to suitably stir and mix the reaction system so as to obtain sufficient dispersion. In this case, the agitating power is generally at least 0.1 kW/m$^3$, and advantageously it is preferably at least 0.2 kW/m$^3$, more preferably at least 0.5 kW/m$^3$ from viewpoint of improvement in quality and yield. There is not particular upper limit, however, it is at most 5 kW/m$^3$ from practical aspect of the stirrer. Therefore, it can be favorably selected within the range generally from 0.1 to 5 kW/m$^3$, and normally from 0.5 to 3 kW/m$^3$.

In the present invention, the molar ratio of an amino acid (1) to N-(1(S)-ethoxycarbonyl-3-phenylpropyl)-L-alanine. N-carboxyanhydride is generally from 0.5 to 5, however, from viewpoint of the quality and productivity of the resulting N-(1(S)-ethoxycarbonyl-3-phenylpropyl)-L-alanyl-amino acid (2), the molar ratio is generally at least 0.7, normally at least 1. As described above, it is suitable that the molar ratio is at least 2 for exhibiting the maximum effect of the present invention. The upper limit thereof is not particularly limited and it is advantageous to be generally at most 5, normally at most 4, particularly at most 3 from viewpoints of economy, load on disposal of waste water, and the like.

The amino acid (1) is preferably added in a whole amount thereof from the start from viewpoint of securing of high yield, simple operability and the like.

The charging concentration of an amino acid (1) is, in terms of the whole amount of the amino acid (1) based on an aqueous liquid, generally from about 5 to about 200% (w/v), though it changes depending on the kind of the amino acid (1). The higher concentration is more advantageous from viewpoints of yield, quality, reaction rate and productivity, and a mixed solvent system of water and an organic solvent having a low miscibility with water and an aqueous liquid essentially consisting of water have higher solubility for a water-soluble substance as compared with a mixed solvent system of water and an organic solvent having a high miscibility with water. Therefore, it has been found that the reaction can be advantageously carried out at a high concentration of at least 10% (w/v), preferably at least 20% (w/v), more preferably at least 30% (w/v) in the case of using, as the solvent for the aqueous liquid, a mixed solvent system of water and an organic solvent having a low miscibility with water or an aqueous liquid essentially consisting of water. For example, in the case of preparing N-(1(S)-ethoxycarbonyl-3-phenylpropyl)-L-alanyl-L-proline (enalapril), it is also possible to carry out the reaction at a high concentration of at least 100% (w/v) as a total amount of L-proline to the aqueous liquid.

The reaction temperature is a temperature at which the reaction mixture is not frozen, normally at most 60° C., preferably at most 50° C., more preferably at most 40° C. When the reaction temperature is too high, a side reaction increases whereby yield and quality tend to lower. For example, the production of N-1(S)-ethoxycarbonyl-3-phenylpropyl)-L-alanyl-L-proline (enalapril) is favorably carried out generally at a temperature within a range of 25±15° C.

After the condensation reaction of N-(1(S)-ethoxycarbonyl-3-phenylpropyl)-L-alanine. N-carboxyanhydride and an amino acid (1), the resulting carbamic acid derivative is decomposed (decarboxylated) under between neutral and acidic condition to produce an N-(1(S)-ethoxycarbonyl-3-phenylpropyl)-L-alanyl-amino acid (2).

The decarboxylation is carried out in an aqueous liquid and the reaction easily proceeds by mixing an acid with the reaction mixture. The decarboxylation is carried out at a temperature at which the reaction mixture is not frozen, normally at most 60° C., preferably at most 50° C., more preferably at most 40° C. When the temperature in decarboxylation is too high, a side reaction increases whereby yield and quality tend to lower. Accordingly, it is generally advantageous to carry out the reaction at a low temperature of, for example, at most 20° C., preferably at most 10° C., in order to reduce the production of a by-product diketopiperazine derivative (3).

Preferably, the decarboxylation is carried out under between neutral and acidic condition paying attention to generated heat and foaming, which differs in the reaction concentration. It is advantageous to adjust the pH of the reaction mixture to normally at most pH 8, preferably at most pH 7, from viewpoint of a decarboxylation rate. And, there is no need to be strongly acidic and generally the pH can be freely selected within a range of from 1 to 6. The pH is finally adjusted to pH 4 to 5, which is a pH near an isoelectric point of N-(1(S)-ethoxycarbonyl-3-phenylpropyl)-L-alanyl-amino acid (2), to produce an N-(1(S)-ethoxycarbonyl-3-phenylpropyl)-L-alanyl-amino acid (2).

The acid used in the decarboxylation reaction is not particularly limited, and preferably it is a strong acid from viewpoint of practical use. Normally a mineral acid such as hydrochloric acid or sulfuric acid is preferable. Hydrochloric acid is more preferable and conc. hydrochloric acid is most preferable. These may be used alone or in admixture thereof. The amount of the acid is such an amount as required to neutralize a basic component in order to adjust the pH to an isoelectric point of an N-(1(S)-ethoxycarbonyl-3-phenylpropyl)-L-alanyl-amino acid (2). The acid can be added to an aqueous liquid containing a reaction mixture, paying attention to generated heat and foaming, or to the acid can be added an aqueous liquid containing a reaction mixture.

The use of preferred basic component and acidic component in between the condensation and the decarboxylation reactions contributes to production of an inorganic salt which is easy of disposal and to improvement of extraction efficiency of N-(1(S)-ethoxycarbonyl-3-phenylpropyl)-L-alanyl-amino acid (2) due to a salting-out effect of the produced inorganic salt. An inorganic salt such as sodium chloride or pottassium chloride has excellent salting-out effect.

In the resulting reaction mixture, the production of a by-product diketopiperazine derivative (3) is suppressed by the presence of water and the N-(1(S)-ethoxycarbonyl-3-phenylpropyl)-L-alanyl-amino acid (2) is stabilized. Preferably, the reaction mixture is quickly subjected to the subsequent step.

According to the reaction process of the present invention, the production of by-products is suppressed in the reaction not only in a mixed solvent system of water and an organic solvent having a high miscibility with water, which has hitherto been regarded as a favorable solvent, but also in a mixed solvent system of water and an organic solvent having a low miscibility with water or in an aqueous liquid essentially consisting of water. Therefore, higher increase in yield of the product (2) can be expected. For example, in the production of N-(1(S)-ethoxycarbonyl-3-phenylpropyl)-L-alanyl-L-proline (enalapril), the reaction yield of at least about 95% can be expected in any of the above-mentioned solvent systems. Such an establishment of higher yield (reduction in impurities) highly contributes to obtaining high quality of an N-(1(S)-ethoxycarbonyl-3-phenylpropyl)-L-alanyl-amino acid (2) or pharmacologically acceptable salt thereof. Further, as described below, if a mixed solvent system of water and an organic solvent having a low miscibility with water or an aqueous liquid essentially consisting of water is suitably used, simplification or omission of extraction operation becomes possible such as no need to replace a solvent in the subsequent extraction operation.

The case for producing N-(1(S)-ethoxycarbonyl-3-phenylpropyl)-L-alanyl-L-proline (enalapril) will be described below.

When N-(1(S)-ethoxycarbonyl-3-phenylpropyl)-L-alanyl-L-proline (enalapril) is produced from L-proline and N-(1(S)-ethoxycarbonyl-3-phenylpropyl)-L-alanine. N-carboxyanhydride, N-(1(S)-ethoxycarbonyl-3-phenylpropyl)-L-alanyl-L-proline having a low content of a diketopiperazine derivative represented by the formula (6):

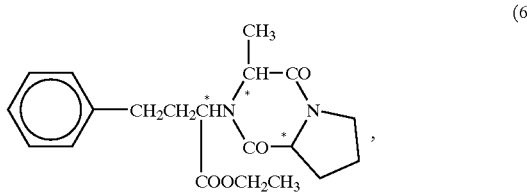

wherein all asymmetric carbon atoms with * have (S)-configuration, N-(1(S)-carboxy-3-phenylpropyl)-L-alanyl-L-proline represented by the formula (7):

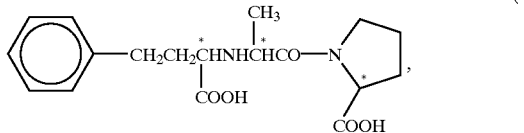

wherein all asymmetric carbon atoms with * have (S)-configuration, and N-(1(S)-ethoxycarbonyl-3-phenylpropyl)-L-alanine represented by the formula (5):

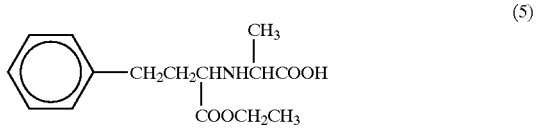

can be obtained by carrying out a condensation by gradually adding at least one of N-(1(S)-ethoxycarbonyl-3-phenylpropyl)-L-alanine. N-carboxyanhydride and a basic pH adjusting agent to an aqueous liquid containing L-proline and, if necessary, N-(1(S)-ethoxycarbonyl-3-phenylpropyl)-L-alanine. N-carboxyanhydride with the pH of the aqueous liquid maintained within a range from 9 to 12 and carrying out a decarboxylation under between neutral and acidic condition.

At least one of N-(1(S)-ethoxycarbonyl-3-phenylpropyl)-L-alanine- N-carboxyanhydride and a basic pH adjusting agent is desirably added over at least ¼ hour. Though there is not particular upper limit, it is at most 20 hours from viewpoint of productivity and the like.

In the reaction in an aqueous liquid essentially consisting of water in which the effect for suppressing the production of a by-product diketopiperazine derivative (3) is maximized, N-(1(S)-ethoxycarbonyl-3-phenylpropyl)-L-alanyl-L-proline having a low content of a diketopiperazine derivative (6), N-(1(S)-carboxy-3-phenylpropyl)-L-alanyl-L-proline (7) and N-(1(S)-ethoxycarbonyl-3-phenylpropyl)-L-alanine (5) can be favorably obtained by a process that N-(1(S)-ethoxycarbonyl-3-phenylpropyl)-L-alanine N-carboxyanhydride is added to an aqueous liquid which contains at least two molar equivalents of L-proline constituting a basic salt based on N-(1(S)-ethoxycarbonyl-3-phenylpropyl)-L-alanine. N-carboxyanhydride, to start the reaction, and condensation is carried out, with maintaining the pH value within a range of from 9 to 12, by gradually adding a basic pH adjusting agent after the pH of the aqueous liquid reaches a range of from 9 to 12 and, then, decarboxylation is carried out.

The above-mentioned aqueous liquid is a medium comprising an organic solvent and water in a weight ratio of 96:4 to 0:100, preferably 20:1 to 0:100, more preferably 10:1 to 0:100. The organic solvent is appropriately selected from the above-mentioned organic solvents having a high miscibility with water and organic solvents having a low miscibility with water, and particularly a halogenated hydrocarbon, a fatty acid ester, a ketone and an ether are preferable. The above-mentioned aqueous liquid may also be substantially water.

The maintained pH of the aqueous liquid in the condensation reaction is within a range of from 9 to 12, preferably within a range of 10.5±1.0, more preferably within a range of 10.5±0.5. By maintaining the pH within the above-mentioned range, the content of the by-products (5) to (7) in the resulting enalapril can be reduced, specifically to less than 5% by weight, preferably to less than 2% by weight.

In the condensation reaction, stirring and mixing are preferably carried out at an agitating power of at least 0.1 kW/m$^3$. Though there is not particular upper limit, it is at most 5 kW/m$^3$ from viewpoint of practical aspect of a stirrer.

Other conditions such as the amount of water to enalapril, the amount of L-proline to N-(1(S)-ethoxycarbonyl-3-phenylpropyl)-L-alanine. N-carboxyanhydride, the charging concentration of L-proline, the kind and amount of a basic pH adjusting agent, and an acid, reaction conditions and reaction method used for a decarboxylation reaction are the same as described for the above-mentioned production of the compound (2).

Thus obtained reaction mixture containing N-(1(S)-ethoxycarbonyl-3-phenylpropyl)-L-alanyl-amino acid (2) after the above-mentioned decarboxylation reaction can be used as it is for formation of a pharmacologically acceptable salt, and alternatively the N-(1(S)-ethoxycarbonyl-3-phenylpropyl)-L-alanyl-amino acid (2) can be once separated before formation of a pharmacologically acceptable salt, taking into consideration of the removal of water-soluble impurities.

Then, a process for separating the N-(1(S)-ethoxycarbonyl-3-phenylpropyl)-L-alanyl-amino acid (2) from a reaction mixture after the decarboxylation reaction will be described below.

For the separation of N-(1(S)-ethoxycarbonyl-3-phenylpropyl)-L-alanyl-amino acid (2) existing in the reaction mixture after the decarboxylation reaction, N-(1(S)-ethoxycarbonyl-3-phenylpropyl)-L-alanyl-amino acid (2) is extracted into an organic solvent using a two-phase medium of the organic solvent and water near isoelectric pH of N-(1(S)-ethoxycarbonyl-3-phenylpropyl)-L-alanyl-amino acid (2). The isoelectric points of N-(1(S)-ethoxycarbonyl-3-phenylpropyl)-L-alanyl-amino acid (2) somewhat differ individually, and is usually near pH 4 to 5. At the isoelectric pH, the solubility of N-(1(S)-ethoxycarbonyl-3-phenylpropyl)-L-alanyl-amino acid (2) into an aqueous solution is minimum. For enhancing an extraction efficiency, it is beneficial to carry out the extraction at a pH within the range of isoelectric point ±2, preferably isoelectric point ±1, more preferably isoelectric point ±0.5. The extraction is carried out in a two-phase system of a water phase and an organic solvent phase, and it is beneficial to remove water-soluble impurities such as the remaining amino acid (1) and produced inorganic salt by transferring them into a water phase and to transfer N-(1(S)-ethoxycarbonyl-3-phenylpropyl)-L-alanyl-amino acid (2) into an organic solvent phase.

The organic solvent used for the extraction is a solvent capable of forming the organic solvent phase constituting a two-phase system together with the water phase, and usually an organic solvent having a low miscibility with water which can be used in the production reaction of the compound (2) is preferably used. As the organic solvent having a low miscibility with water, a halogenated hydrocarbon, a fatty acid ester, a ketone and an ether are preferred as described above, and among these, a fatty acid ester, particularly an acetate, more particularly ethyl acetate is preferable from viewpoints of easy handling, safety of the solvent, cost of the solvent, use advantage as a solvent in the formation of a pharmacologically acceptable salt, high effect for stabilizing N-(1(S)-ethoxycarbonyl-3-phenylpropyl)-L-alanyl-amino acid (2) (effect for suppressing the production of diketopiperazine derivative (3)) and the like.

Therefore, when the production reaction of the compound (2) in the present invention is carried out in a two-phase medium of water and an organic solvent having a low miscibility with water, it is possible that the water phase is separated with carrying out the decarboxylation or after the decarboxylation to obtain a solution comprising the organic solvent used for the production reaction of N-(1(S)-ethoxycarbonyl-3-phenylpropyl)-L-alanyl-amino acid (2). By this there can be simply and efficiently obtained an organic solvent phase containing N-(1(S)-ethoxycarbonyl-3-phenylpropyl)-L-alanyl-amino acid (2). The N-(1(S)-ethoxycarbonyl-3-phenylpropyl)-L-alanyl-amino acid (2) remaining in the water phase can be recovered, if necessary, by extracting with the above-mentioned organic solvent. Further, the resulting organic solvent phase can be washed with water, if necessary.

When the amount of water in an aqueous liquid containing N-(1(S)-ethoxycarbonyl-3-phenylpropyl)-L-alanyl-amino acid (2) is controlled through this extraction and separation operation so that the weight ratio of organic solvent to water is 96:4 as a whole or the proportion of water is higher than the above ratio, the production of by-products such as a diketopiperazine derivative (3) can be suppressed. By this, the production of by-products can be at least suppressed to at most ½ to ⅓ such as in Examples 8 and 10 described below. Needless to say, this suppression effect is higher when the water content is higher, and the proportion of water is higher preferably than the weight ratio of organic solvent to water of 96:4.

The above-mentioned extraction operation and washing operation are carried out at a temperature of at most the boiling point of a solvent and at which the solvent is not frozen though the temperature depends on the kind of the solvent and operation time. Particularly higher temperature is not required, and the operations are carried out, practically at a temperature at which the solution is not frozen generally at most 60° C., normally at most 50° C., preferably at most 40° C. For minimizing production of a by-product diketopiperazine derivative (3), it is generally advantageous to carry out the above-mentioned operations, for example, at a lower temperature of at most 20° C., preferably at most 10° C.

However, it has been found that especially when the N-(1(S)-ethoxycarbonyl-3-phenylpropyl)-L-alanyl-amino acid (2) is N-(1(S)-ethoxycarbonyl-3-phenylpropyl)-L-alanyl-L-proline (enalapril) having high water-solubility, partition into an organic solvent phase can be accomplished extremely efficiently by carrying out the above-mentioned operations at a higher temperature. For example, the partition ratio of N-(1(S)-ethoxycarbonyl-3-phenylpropyl)-L-alanyl-L-proline (enalapril) in a two-phase system of a water phase and an organic solvent phase highly depends on temperature, and higher partition ratio into an organic solvent phase is obtained at a temperature range of at least 20° C., preferably at least 25° C., more preferably at least 30° C. The improvement of this partition ratio into an organic solvent phase at a higher temperature exerts a large effect especially when the amount of an organic solvent is small and when using an organic solvent revealing not necessarily excellent extraction efficiency for N-(1(S)-ethoxycarbonyl-3-phenylpropyl)-L-alanyl-L-proline (enalapril), for example, an acetate such as ethyl acetate.

The upper limit of the above-mentioned operation temperature is variable with an operation mode such as continuous extraction or batchwise extraction and is not particularly restricted, however, it is not particularly required to be higher, and is practically at most 60° C., normally at most 50° C., preferably at most 40° C.

Conventionally, in extracting N-(1(S)-ethoxycarbonyl-3-phenylpropyl)-L-alanyl-L-proline (enalapril), extremely troublesome operations are required such as utilization of salting-out effect and use of a large amount of an extraction solvent due to high water-solubility of enalapril. However, according to the present invention, a solution of an organic solvent containing N-(1(S)-ethoxycarbonyl-3-phenylpropyl)-L-alanyl-L-proline (enalapril) can be simply and efficiently obtained in high yield and high quality by carrying out the operation under the above-mentioned temperature condition, without a treatment for saturating a water phase with a large amount of a salt and without a multiple extraction with a large amount of an organic solvent.

When the reaction is carried out using an organic solvent having a high miscibility with water, the organic solvent is removed and then substituted with an organic solvent having a low miscibility with water and the same operations such as washing with water are carried out under the same condition.

Further, by carrying out an operation at a low temperature, normally at a temperature of less than 20° C., preferably at a temperature of less than 10° C. in a two-phase medium of water and an organic solvent having a low miscibility with water by utilizing the above-mentioned partition behavior, it is possible to efficiently partition N-(1(S)-ethoxycarbonyl-3-phenylpropyl)-L-alanyl-L-proline (enalapril) reversely into the water phase, and to efficiently extract impurities having a low water-solubility such as a diketopiperazine derivative (3) into the organic phase by washing the water phase with an organic solvent. In this case, there is preferably used a method in which N-(1(S)-ethoxycarbonyl-3-phenylpropyl)-L-alanyl-L-proline (enalapril) is extracted into water from the above-mentioned solution of an organic solvent containing N-(1(S)-ethoxycarbonyl-3-phenylpropyl)-L-alanyl-L-proline (enalapril) from which the water-soluble impurities have been removed.

Namely, if a two-phase medium of water and an organic solvent having a low miscibility with water containing N-(1(S)-ethoxycarbonyl-3-phenylpropyl)-L-alanyl-L-proline is separated at a temperature of at least 20° C., N-(1(S)-ethoxycarbonyl-3-phenylpropyl)-L-alanyl-L-proline can be transferred into the organic solvent phase, or if the two-phase medium is separated at a temperature of less than 20° C., N-(1(S)-ethoxycarbonyl-3-phenylpropyl)-L-alanyl-L-proline can be transferred into the water phase. Thus, N-(1(S)-ethoxycarbonyl-3-phenylpropyl)-L-alanyl-L-proline can be separated. Especially, the case in which the organic solvent is an acetate is preferable from the viewpoints of easy handling, safety of the solvent, and high effect for stabilizing N-(1(S)-ethoxycarbonyl-3-phenylpropyl)-L-alanyl-L-proline. Further, even when the above-mentioned two-phase medium is separated at a temperature of at least 20° C., N-(1(S)-ethoxycarbonyl-3-phenylpropyl)-L-alanyl-L-proline can be transferred into the organic solvent phase without saturating the water phase with an inorganic salt.

Then the explanation is given below as to an operation, which is carried out in the coexistence of water, for forming a pharmacologically acceptable salt from N-(1(S)-ethoxycarbonyl-3-phenylpropyl)-L-alanyl-amino acid (2) in a reaction mixture, extracted solution or washing solution containing N-(1(S)-ethoxycarbonyl-3-phenylpropyl)-L-alanyl-amino acid (2).

The existence of water contributes to not only suppression of the production of a by-product diketopiperazine derivative (3) from N-(1(S)-ethoxycarbonyl-3-phenylpropyl)-L-alanyl-amino acid (2), but also to suppression of the production of a by-product diketopiperazine derivative (3) from the resulting pharmacologically acceptable salt.

A reaction mixture, extracted solution or washing solution containing N-(1(S)-ethoxycarbonyl-3-phenylpropyl)-L-alanyl-amino acid (2) obtained by another procedure can also be used for the formation of a pharmacologically acceptable salt.

During the formation and separation operation of this salt, the weight ratio of an organic solvent and water is controlled so as to be in the range from 96:4 to 0:100 as in the above-mentioned reaction and separation operation. Dehydration of a solution containing N-(1(S)-ethoxycarbonyl-3-phenylpropyl)-L-alanyl-amino acid (2) by addition of a dehydrating agent or concentration operation rather invites disadvantage of production of a by-product diketopiperazine derivative (3).

In the present invention, the following procedures are also contemplated:

a pharmacologically acceptable salt of N-(1(S)-ethoxycarbonyl-3-phenylpropyl)-L-alanyl-amino acid (2) is formed in a medium comprising an organic solvent and water in a weight ratio of 96:4 to 0:100 which medium contains N-(1(S)-ethoxycarbonyl-3-phenylpropyl)-L-alanyl-amino. acid (2), which N-(1(S)-ethoxycarbonyl-3-phenylpropyl)-L-alanyl-amino acid (2) has been transferred into either one phase and separated by extracting from a reaction mixture after reaction containing the product (2) in the manner as described above using a two-phase medium comprising water and an organic solvent having a low miscibility with water, a pharmacologically acceptable salt of N-(1(S)-ethoxycarbonyl-3-phenylpropyl)-L-alanyl-amino acid (2) is formed in an organic solvent phase in which water coexists and which phase is obtained by extracting or washing a reaction mixture containing N-(1(S)-ethoxycarbonyl-3-phenylpropyl)-L-alanyl-amino acid (2) using a medium comprising an organic solvent and water in which a weight ratio of the organic solvent: water is from 96:4 to 0:100, or in a water phase obtained by extracting or washing a reaction mixture containing N-(1(S)-ethoxycarbonyl-3-phenylpropyl)-L-alanyl-amino acid (2) using the above-mentioned medium, and, if necessary, the pharmacologically acceptable salt is isolated, and using a two-phase liquid comprising water and an organic solvent having a low miscibility with water, N-(1(S)-ethoxycarbonyl-3-phenylpropyl)-L-alanyl-L-proline is transferred into the organic solvent phase by separating the two-phase liquid at a temperature of at least 20° C., or is transferred into the water phase by separating the two-phase liquid at a temperature of less than 20° C. and a pharmacologically acceptable salt thereof is formed in the organic solvent phase or the water phase, and isolated.

The solvent used for the formation of the pharmacologically acceptable salt is basically the same as that used for the production reaction of the compound (2). The preferable kind of the solvent and the ratio of the organic solvent and water differ depending on a solubility of N-(1(S)-ethoxycarbonyl-3-phenylpropyl)-L-alanyl-amino acid (2) to be used. However, the solvents shown in the description of the reaction can be used, in general. The ratio of organic solvent:water and molar ratio of the product (2) to water are also the same as those for the production reaction of the compound (2).

The formation of a pharmacologically acceptable salt can be easily carried out by mixing N-(1(S)-ethoxycarbonyl-3-phenylpropyl)-L-alanyl-amino acid (2) with an inorganic acid such as hydrochloric acid, sulfuric acid or phosphoric acid, an organic acid such as acetic acid, maleic acid, fumaric acid, tartaric acid or citric acid, or an amino acid such as glycine or phenylalanine, in an aqueous liquid. The mixing method is not particularly limited, and examples thereof are, for example, a method in which the above-mentioned inorganic acid, organic acid or amino acid is added to an aqueous liquid containing N-(1(S)-ethoxycarbonyl-3-phenylpropyl)-L-alanyl-amino acid (2), a method in which an aqueous liquid containing N-(1(S)-ethoxycarbonyl-3-phenylpropyl)-L-alanyl-amino acid (2) is added to an aqueous liquid of the above-mentioned inorganic acid, organic acid or amino acid, and the like.

The amount used of the above-mentioned inorganic acid, organic acid or amino acid is not particularly limited, and in general, when no substance having adverse influence exists, it may advantageously be approximately a theoretical amount required based on N-(1(S)-ethoxycarbonyl-3-phenylpropyl)-L-alanyl-amino acid (2). In a solvent having a relatively high solubility for a pharmacologically acceptable salt of N-(1(S)-ethoxycarbonyl-3-phenylpropyl)-L-alanyl-amino acid (2), and the like, the equilibrium of salt formation can be shifted by using an excess amount thereof to increase a deposition ratio of a salt. It is advantageous from economical viewpoint and the like to use them, for example, in an amount of 0.9 to 2.5 fold, preferably 0.95 to 2.0 fold, more preferably 0.95 to 1.2 fold of the theoretical amount.

When N-(1(S)-ethoxycarbonyl-3-phenylpropyl)-L-alanyl-amino acid (2) includes an isomer, for example, when the carbon atom in the formula (2) to which a ethoxycarbonyl group is connected is an asymmetric carbon atom, the above-mentioned inorganic acid, organic acid or amino acid can be used in approximately the theoretical amount required, for example, in an amount of 0.9 to 1.2 fold, preferably 0.95 to 1.1 fold of the theoretical amount based on the isomer having favorable antihypertensive action in which said carbon atom has (S)-configuration.

It is preferable to form the pharmacologically acceptable salt in an aqueous liquid essentially consisting of water because, in particular, effect for suppressing the production of a diketopiperazine derivative (3) is remarkably high, and contamination of an organic solvent which is not preferable for a human body into the final product is avoided. However, it turns out that, when the N-(1(S)-ethoxycarbonyl-3-phenylpropyl)-L-alanyl-amino acid (2) is N-(1(S)-ethoxycarbonyl-3-phenylpropyl)-L-alanyl-L-proline and the pharmacologically acceptable salt thereof is maleic acid salt, there are problems for the production in an industrial scale that high yield is not easily obtained and property and condition of the produced crystal deteriorate and adverse influence is exerted on filtration property and drying property since the water-solubility of the maleate is rather high even at low temperature. Furthermore, any satisfactory method to solve the problems has not been known hitherto.

Then, it has been found that these problems can be favorably solved by adding and/or allowing to coexist an inorganic salt having high salting-out effect, particularly sodium chloride, potassium chloride or the like, by carrying out the steps of forming and crystallizing a salt within a range of 40 to 70° C., or by employing these methods alone or in combination thereof.

Especially when a pharmacologically acceptable salt is formed from a reaction solution which is obtained by condensing an amino acid (1) and N-(1(S)-ethoxycarbonyl-3-phenylpropyl)-L-alanine. N-carboxyanhydride in an aqueous liquid essentially consisting of water, the yield of the pharmacologically acceptable salt can be increased due to the salting-out effect of an inorganic salt derived from a pH adjusting agent even without adding a further inorganic salt. Particularly, in the case of a reaction solution obtained by carrying out condensation at a high reaction concentration of at least 10% (w/v), preferably at least 20% (w/v), more preferably at least 30% (w/v), the concentration of the inorganic salt derived from a pH adjusting agent is necessarily increased and therefore higher salting-out effect can be expected.

When N-(1(S)-ethoxycarbonyl-3-phenylpropyl)-L-alanyl-L-proline maleate (enalapril maleate) is formed in an aqueous liquid in which a large amount of a water-soluble inorganic salt generated from the production reaction of the compound (2) is dissolved, there is a tendency that the solubility of N-(1(S)-ethoxycarbonyl-3-phenylpropyl)-L-alanyl-L-proline and maleic acid in the above-mentioned aqueous liquid decreases and then the formation of the maleate becomes incomplete, resulting in decrease of the yield and remaining and contamination of maleic acid which is an insoluble component. Further, the property and condition of the resulting crystal are generally poor, and adverse influence is exerted also on filtration property and drying property. Thus, it is important that the concentration of an inorganic salt is not too high in the steps of forming and crystallizing a maleate. The upper limit of the inorganic salt concentration at the formation and crystallization of the salt cannot be stipulated unconditionally since it depends on the concentration, temperature and method in operation and the kind of an inorganic salt and the like. The concentration is generally at most 15% by weight, preferably at most 10% by weight for suitable operation.

From the above-mentioned viewpoints, for preferably solving these problems, there can be used a method in which an aqueous liquid of N-(1(S)-ethoxycarbonyl-3-phenylpropyl)-L-alanyl-L-proline (enalapril) in which an inorganic salt coexists is gradually added to an aqueous liquid containing maleic acid. By this method, unexpectedly salt formation can be carried out with excellent yield and quality without using a large amount of maleic acid. According to this method, the crystallization amount can be advantageously raised by enhancement of salting-out effect due to phenomenon in which the inorganic salt concentration is low in initial stage of a salt formation and the inorganic salt concentration is finally increased. Though sufficient crystallization amount can be usually obtained by this operation, it is also possible to newly add an inorganic salt to increase the crystallization amount according to demands. Regarding removal of impurities, N-(1(S)-carboxy-3-phenylpropyl)-L-alanyl-L-proline (7) and N-(1(S)-ethoxycarbonyl-3-phenylpropyl)-L-alanine (5) can be advantageously removed, and consequently, N-(1(S)-ethoxycarbonyl-3-phenylpropyl)-L-alanyl-L-proline can be obtained having a low content of these impurities.

The time for addition of the aqueous liquid of enalapril in which an inorganic salt coexists is not particularly limited and, in general, the time required for adding the whole amount thereof is at least ¼ hour, normally at least ⅓ hour, preferably at least ½ hour. The amount of maleic acid used is 0.9 to 3.0 molar equivalents, preferably 0.95 to 2.0 molar equivalents, more preferably 0.95 to 1.2 molar equivalents, based on enalapril.

The operation temperature for forming the pharmacologically acceptable salt of the present invention depends on the kind of a solvent, the kind of a salt formed, an operation manner and the like, and cannot be particularly limited, however, it is carried out preferably at 40 to 70° C., and it is suitably carried out more preferably at 50 to 70° C., particularly about 60° C. A system in which water coexists is particularly important since heating in a system in which no water coexists leads to the production of the by-product diketopiperazine derivative (3). The salt formation at lower temperature is not preferable because a fine crystal is deposited and slurry in the form of whip is formed to deteriorate fluidity and filterability, and the resulting crystal has a high liquid content and cannot be easily dried, and the like. Though these problems can be advantageously improved by raising the salt formation temperature as described above, it has been found that raising of the salt formation temperature is also preferable for improving a property of removing impurities. As to an advantageous method for raising the salt formation temperature, the method in which N-(1(S)-ethoxycarbonyl-3-phenylpropyl)-L-alanyl-L-proline (enalapril) is gradually added to the aqueous liquid of maleic acid as described above is preferable also from a viewpoint that the thermal histeresis on enalapril before the salt formation can be reduced. Further, increase in the proportion of water in an aqueous liquid used is also advantageous since it further enhances the effect for suppressing the production of the by-product diketopiperazine derivative (3). Finally, the reaction mixture can be cooled to a temperature of at most 20° C., preferably at most 10° C. to increase the amount crystallized.

Particularly, in a method for converting N-(1(S)-ethoxycarbonyl-3-phenylpropyl)-L-alanyl-L-proline (enalapril) to its maleate, the amount crystallized of N-(1(S)-ethoxycarbonyl-3-phenylpropyl)-L-alanyl-L-proline maleate can be increased by adding and/or allowing to coexist an inorganic salt such as sodium chloride or potassium chloride in an aqueous liquid containing N-(1(S)-ethoxycarbonyl-3-phenylpropyl)-L-alanyl-L-proline and maleic acid. The aqueous liquid is preferably a medium comprising an organic solvent and water in a weight ratio of from 96:4 to 0:100. As the above-mentioned organic solvent, the one usable for the production reaction of the compound (2) as described above can be suitably used. The amount of water to enalapril can be the same as that for the above-mentioned compound (2). The amount of maleic acid is 0.9 to 3.0 molar equivalents, preferably 0.95 to 2.0 molar equivalents, more preferably 0.95 to 1.2 molar equivalents, based on enalapril.

Thus obtained pharmacologically acceptable salt of N-(1(S)-ethoxycarbonyl-3-phenylpropyl)-L-alanyl-amino acid (2) can be, if necessary, purified, for example, according to a method such as recrystallization or reslurry washing. The reslurry washing means a method in which a crystal is added to a medium and stirred in the form of slurry and filtrated for purification. A trace amount of a by-product diketopiperazine derivative (3) is produced also from the N-(1(S)-ethoxycarbonyl-3-phenylpropyl)-L-alanyl-amino acid (2) which has been stabilized as a salt, however, the production of diketopiperazine derivative (3) can be suppressed by carrying out this purification operation in an aqueous liquid. Namely, the existence of water suppresses the production of a by-product diketopiperazine derivative (3) also in this purification operation.

Furthermore, as described above, for increasing the yield, the addition of an inorganic salt can be suitably carried out, and the operation temperatures for recrystallization and reslurry washing can be raised, and preferably the operation can be carried out at a temperature in the range from 40 to 70° C., and can be suitably carried out more preferably at from 50 to 70° C., particularly about 60° C., from viewpoint of improving the property and condition of the resulting slurry and crystal, as described above.

By such operations, an N-(1(S)-carboxy-3-phenylpropyl)-L-alanyl-amino acid (4) and N-(1(S)-ethoxycarbonyl-3-phenylpropyl)-L-alanine (5) can be advantageously reduced and, consequently, an N-(1(S)-ethoxycarbonyl-3-phenylpropyl)-L-alanyl-amino acid (2) having a low content of these impurities can be obtained. This impurity removing effect differs depending on the purification method and the kind of solvent, and cannot be generally defined and, for example, the amount of impurities can be lowered to a level of at most 1/10, preferably to a level at which the content in the resulting salt is negligible, as described in Example 9 shown below. The above-mentioned aqueous liquid is preferably a medium comprising an organic solvent and water in a weight ratio of 96:4 to 0:100. As the above-mentioned organic solvent, that which can be used for the production reaction of the compound (2) as described above can be suitably used.

The by-product diketopiperazine derivative (3) once produced by an operation in a dehydrated solution does not easily regenerate the N-(1(S)-ethoxycarbonyl-3-phenylpropyl)-L-alanyl-amino acid (2) and a pharmacologically acceptable salt thereof even if water is added thereafter.

A most preferable embodiment of the present invention is a process for preparing a pharmacologically acceptable salt of N-(1(S)-ethoxycarbonyl-3-phenylpropyl)-L-alanyl-amino acid (2) which comprises reacting an amino acid (1) and N-(1(S)-ethoxycarbonyl-3-phenylpropyl)-L-alanine. N-carboxyanhydride in an aqueous liquid essentially consisting of water under the above-mentioned conditions, subsequently forming a pharmacologically acceptable salt thereof from the reaction mixture containing the resulting N-(1(S)-ethoxycarbonyl-3-phenylpropyl)-L-alanyl-amino acid (2), without extracting the product (2).

Another most preferable embodiment of the present invention is a process for preparing a pharmacologically acceptable salt of N-(1(S)-ethoxycarbonyl-3-phenylpropyl)-L-alanyl-amino acid (2) which comprises reacting an amino acid (1) and N-(1(S)-ethoxycarbonyl-3-phenylpropyl)-L-alanine. N-carboxyanhydride in a mixed solvent system of water and an organic solvent having a low miscibility with water or in an aqueous liquid essentially consisting of water under the above-mentioned specific conditions, extracting and separating N-(1(S)-ethoxycarbonyl-3-phenylpropyl)-L-alanyl-amino acid (2) from the resulting reaction mixture to obtain a water-saturated organic solvent phase containing N-(1(S)-ethoxycarbonyl-3-phenylpropyl)-L-alanyl-amino acid (2), then forming a pharmacologically acceptable salt thereof.

From thus obtained pharmacologically acceptable salt of N-(1(S)-ethoxycarbonyl-3-phenylpropyl)-L-alanyl-amino acid (2), a crystal can be separated according to a method such as centrifugal separation, pressure filtration or filtration under reduced pressure, and washed, and dried under normal pressure or reduced pressure.

The present invention is more specifically explained below by means of Examples. It is to be understood that the present invention is not limited only to those Examples.

The HPLC analysis was carried out under the following conditions:

Column: FINEPAK SIL C18-5(Trade name, 4.6 mm×25 cm, available from JASCO CORP.)

Eluent: 0.1 M $KH_2PO_4$(pH2.8)/$CH_3CN$ (70:30(V/V))

Flow rate: 1.0 ml/min

Temperature: 45° C.

Detection condition: UV 210 nm

EXAMPLE 1

To 22.02 g (191 mmol) of L-proline were added 20 ml of ethyl acetate and 22 ml of $H_2O$ and, then, the pH was adjusted to 10.5 with 30% by weight NaOH aqueous solution. The inner temperature was regulated to 19 to 20° C. and, then, thereto was slowly added dropwise a solution containing 29.20 g (96 mmol) of N-(1(S)-ethoxycarbonyl-3-phenylpropyl)-L-alanine. N-carboxyanhydride in 156 ml of ethyl acetate over 4 hours with stirring. During the dropping, the reaction mixture was maintained at a pH of 10.5±0.5 with adding dropwise 30% by weight NaOH aqueous solution, and simultaneously, the inner temperature was maintained at 19 to 20° C. and the agitating power was maintained at 1 kW/$m^3$. After completion of the dropping, the stirring was continued for 1 hour under the same conditions. The inner temperature was raised to 30° C., and the pH thereof was adjusted to 4.5±0.2 with 35% by weight HCl. Under the same conditions, the stirring was continued for 10 minutes to complete the decarboxylation. The organic phase was separated at 30° C. and, then, the water phase was further extracted once with 20 ml of ethyl acetate at 30° C. The resulting organic phases were mixed and then washed once with $H_2O$ in an amount of 5% by volume of the organic phase at 30° C. The water-saturated organic phase was analyzed with HPLC and, as a result, a solution containing 14% by weight N-(1(S)-ethoxycarbonyl-3-phenylpropyl)-L-alanyl-L-proline was obtained. The reaction ratio was 97% and the extraction recovery was 96% (both were calculated by HPLC absolute calibration curve method. Hereinafter the same). The amounts produced of the by-products were as follows: diketopiperazine derivative (3) 0.5% by weight, carboxy derivative (4) 0.4% by weight, N-(1(S)-ethoxycarbonyl-3-phenylpropyl)-L-alanine (5) 0.5% by weight.

Further, to this solution was added 10.49 g (90 mmol) of maleic acid with stirring at an inner temperature of 30° C. The stirring was continued for 1 hour under the same conditions and, then, the inner temperature was cooled down to 5° C. over 3 hours, and the stirring was continued for further 2 hours. The deposited crystal was taken out by filtration under reduced pressure, and washed twice with 80 ml of ethyl acetate cooled to 5° C. The resulting wet crystal was dried under reduced pressure (20 to 50° C., 30→1 mmHg), to obtain 42.54 g (86 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine N-carboxyanhydride was 90%.

EXAMPLE 2

To 40 ml of $H_2O$ was added 22.02 g (191 mmol) of L-proline and, then, the pH was adjusted to 10.5 with 30% by weight NaOH aqueous solution. The inner temperature was regulated to 19 to 20° C. and, then, thereto was slowly added 29.20 g (96 mmol) of a crystal of N-(1(S)-ethoxycarbonyl-3-phenylpropyl)-L-alanine. N-carboxyanhydride over 6 hours with stirring. During the addition, the reaction mixture was maintained at a pH of 10.5±0.5 with adding dropwise 30% by weight NaOH aqueous solution, and simultaneously, the inner temperature was maintained at 19 to 20° C. and the agitating power was maintained at 1.2 $kW/m^3$. After completion of the addition, the stirring was continued for 1 hour under the same conditions. The inner temperature was raised to 30° C. and the pH thereof was adjusted to 4.2±0.2 with 35% by weight HCl. Then, under the same conditions, the stirring was continued for 10 minutes to complete the decarboxylation. The reaction mixture was analyzed with HPLC and, as a result, a solution containing 21% by weight N-(1(S)-ethoxycarbonyl-3-phenylpropyl)-L-alanyl-L-proline was obtained. The reaction ratio was 97% and the amounts produced of the by-products were as follows: diketopiperazine derivative (3) at most 0.05% by weight, carboxy derivative (4) 0.4% by weight, N-(1(S)-ethoxycarbonyl-3-phenylpropyl)-L-alanine (5) 0.6% by weight.

This solution containing N-(1(S)-ethoxycarbonyl-3-phenylpropyl)-L-alanyl-L-proline was added to a solution of 10.66 g (92 mmol) of maleic acid in 20 ml of $H_2O$, with stirring at an inner temperature of 60° C. over 1 hour. The stirring was continued for 1 hour under the same conditions and, then, the inner temperature was cooled down to 5° C. over 3 hours, and the stirring was continued for further 2 hours. The deposited crystal was taken out by filtration under reduced pressure, and quickly washed three times with 80 ml of $H_2O$ cooled to 0 to 3° C. . The resulting crystal had a good filterability and a glossy and excellent crystal form; In the case of forming the salt at an inner temperature of 30° C., the resulting salt was slurry in the form of whip and had a poor filterability and a form of fine crystal. The resulting wet crystal was dried under reduced pressure (20 to 50° C., 30→1 mmHg), to obtain 42.05 g (85 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine N-carboxyanhydride was 89%.

EXAMPLE 3

To 22 ml of $H_2O$ was added 22.02 g (191 mmol) of L-proline and, then, to this L-proline aqueous solution was added a solution containing 29.20 g (96 mmol) of N-(1(S)-ethoxycarbonyl-3-phenylpropyl)-L-alanine. N-carboxyanhydride in 176 ml of ethyl acetate. The inner temperature was regulated to 19 to 20° C. and, then, the reaction mixture was maintained at a pH of 10.5±1.0 with adding dropwise 30% by weight NaOH aqueous solution for 5 hours under stirring, and simultaneously, the agitating power was maintained at 1 kW/m3. The inner temperature was raised to 30° C. and the pH thereof was adjusted to 4.5±0.2 with 35% by weight HCl. Then, under the same conditions, the stirring was continued for 10 minutes to complete the decarboxylation. The organic phase was separated at 30° C. and, then, the water phase was further extracted once with 20 ml of ethyl acetate at 30° C. . The organic phases were mixed and, then washed once with $H_2O$ in an amount of 5% by volume of the organic phase at 30° C. The water-saturated organic phase was analyzed with HPLC and, as a result, a solution containing 14% by weight N-(1(S)-ethoxycarbonyl-3-phenylpropyl)-L-alanyl-L-proline was obtained. The reaction ratio was 96% and the extraction ratio was 96%. The amounts produced of the by-products were as follows: diketopiperazine derivative (3) 0.4% by weight, carboxy derivative (4) 0.5% by weight, N-(1(S)-ethoxycarbonyl-3-phenylpropyl)-L-alanine (5) 0.6% by weight.

Further, to this solution was added a solution of 10.25 g (88 mmol) of maleic acid in 20 ml of $H_2O$, with stirring at an inner temperature of 30° C. The stirring was continued for 1 hour under the same conditions and, then, the inner temperature was cooled down to 5° C. over 3 hours, and the stirring was continued for further 2 hours. The deposited crystal was taken out by filtration under reduced pressure, and washed twice with 80 ml of ethyl acetate cooled to 5° C. The resulting wet crystal was dried under reduced pressure (20 to 50° C., 30→1 mmHg), to obtain 41.67 g (85 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 88%.

EXAMPLE 4

To 22.02 g (191 mmol) of L-proline and 29.20 g 96 mmol) of N-(1(S)-ethoxycarbonyl-3-phenylpropyl)-L-alanine. N-carboxyanhydride was added 60 ml of $H_2O$. The inner temperature was regulated to 19 to 20° C. and, then, the reaction mixture was maintained at a pH of 10.5±1.0 with adding dropwise 30% by weight NaOH aqueous solution for 6 hours under stirring, and simultaneously, the agitating power was maintained at 0.9 $kW/m^3$. The inner temperature was raised to 30° C. and the pH thereof was adjusted to 4.2±0.2 with 35% by weight HCl. After adjusting of pH, under the same conditions, the stirring was continued for 10 minutes to complete the decarboxylation. The reaction mixture was analyzed with HPLC and, as a result, a solution containing 18% by weight N-(1(S)-ethoxycarbonyl-3-phenylpropyl)-L-alanyl-L-proline was obtained. The reaction ratio was 96%, and the amounts produced of the by-products were as follows: diketopiperazine derivative (3) at most 0.05% by weight, carboxy derivative (4) 0.4% by weight, N-(1(S)-ethoxycarbonyl-3-phenylpropyl)-L-alanine (5) 0.7% by weight.

To this solution was added a solution wherein 21.09 g (182 mmol) of maleic acid was dissolved in 40 ml of $H_2O$, with stirring at an inner temperature of 30° C. The stirring was continued for 1 hour under the same conditions and, then, the inner temperature was cooled down to 5° C. over 3 hours, and the stirring was continued for further 2 hours. The deposited crystal was taken out by filtration, and quickly washed twice with 20 ml of $H_2O$ cooled to 0 to 3° C. The resulting wet crystal was dried under reduced pressure (20 to 50° C., 30→1 mmHg), to obtain 41.29 g (84 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 87%.

EXAMPLE 5

To 60 ml of $H_2O$ was added 22.02 g (191 mmol) of L-proline and, then, 25.47 g (191 mmol) of 30% by weight NaOH aqueous solution was added thereto with stirring. At this time, the pH of the solution is 12.9. The inner temperature was regulated to 14 to 15° C. and, then, thereto was added 29.20 g (96 mmol) of N-(1(S)-ethoxycarbonyl-3-phenylpropyl)-L-alanine. N-carboxyanhydride over 30 minutes with stirring. After the completion of the addition, the pH of the reaction mixture became approximately 10 in 30 minutes, and for 8 hours from this time, the reaction mixture was maintained at a pH of 10.0±0.5 with adding dropwise 30% by weight NaOH aqueous solution, and simultaneously, the agitating power was maintained at 0.9 kW/m³ to complete the reaction. With the inner temperature maintained at 15° C., the pH was adjusted to 4.0±0.2 with 35% by weight HCl. After adjusting the pH, under the same conditions, the stirring was continued for 10 minutes to complete the decarboxylation. The reaction mixture was analyzed with HPLC and, as a result, a solution containing 18% by weight N-(1(S)-ethoxycarbonyl-3-phenylpropyl)-L-alanyl-L-proline was obtained. The reaction ratio was 99% and the amounts produced of the by-products were as follows: diketopiperazine derivative (3) 0.05% by weight, carboxy derivative (4) 0.1% by weight, N-(1(S)-ethoxycarbonyl-3-phenylpropyl)-L-alanine (5) 0.6% by weight.

This solution containing N-(1(S)-ethoxycarbonyl-3-phenylpropyl)-L-alanyl-L-proline was added to a solution. prepared by dissloving 11.31 g (97 mmol) of maleic acid in 20 ml of $H_2O$, with stirring at an inner temperature of 60° C. over 1 hour. The stirring was continued for 1 hour under the same conditions and, then, the inner temperature was cooled down to 5° C. over 3 hours, and the stirring was continued for further 1 hour. The deposited crystal was taken out by filtration, and quickly washed twice with 80 ml of $H_2O$ cooled to 0 to 3° C. The resulting crystal had a good filterability, a glossy and excellent crystal form; In the case of forming the salt at an inner temperature of 30° C., the resulting salt was slurry in the form of whip and had a poor filterability and a form of fine crystal. The resulting wet crystal was dried under reduced pressure (20 to 50° C., 30→1 mmHg), to obtain 42.52 g (86 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 90%.

EXAMPLE 6

According to Example 1, using various solvents shown in Table 1, N-(1(S)-ethoxycarbonyl-3-phenylpropyl)-L-alanyl-L-proline was prepared and applicability of the various solvents was examined. The reaction ratios in various solvents are shown in Table 1.

TABLE 1

| Miscibility of organic solvent with water | Solvents | Reaction ratio (%) |
| --- | --- | --- |
| Low | Ethyl acetate/$H_2O$ | 98 |
|  | Methylene chloride/$H_2O$ | 96 |
|  | Methyl isobutyl ketone/$H_2O$ | 95 |
|  | Methyl isopropyl ketone/$H_2O$ | 95 |
| High | $CH_3CN/H_2O$ | 95 |
|  | THF/$H_2O$ | 96 |
| — | $H_2O$ | 97 |

EXAMPLE 7

According to Example 1 except that the pH was changed as shown in Table 2, N-(1(S)-ethoxycarbonyl-3-phenylpropyl)-L-alanyl-L-proline was synthesized and the influence of pH was investigated. The reaction ratio at each pH and the amounts produced (% by weight) of the diketopiperazine derivative (3), N-(1(S)-carboxy-3-phenylpropyl)-L-alanyl-L-proline (carboxy derivative (4)) and N-(1(S)-ethoxycarbonyl-3-phenylpropyl)-L-alanine (ALE (5)) are shown in Table 2. The control of pH was within the range of ±1.0.

TABLE 2

| pH | Reaction ratio (%) | Amount produced of diketopiperazine derivative (3) (% by weight) | Amount produced of carboxy derivative (4) (% by weight) | Amount produced of ALE (5) (% by weight) |
| --- | --- | --- | --- | --- |
| 8.0 | 84 | 0.3 | 0.0 | 9.5 |
| 9.0 | 95 | 0.4 | 0.0 | 4.2 |
| 10.5 | 98 | 0.5 | 0.4 | 0.6 |
| 12.0 | 95 | 0.5 | 1.5 | 0.3 |
| 13.0 | 90 | 0.4 | 5.5 | 0.2 |

EXAMPLE 8

According to Example 1, an ethyl acetate solution of N-(1(S)-ethoxycarbonyl-3-phenylpropyl)-L-alanyl-L-proline was prepared. 129.40 Grams of this organic phase was washed twice with 30 ml of saturated brine, and dehydrated with magnesium sulfate. The solvent was concentrated and, then, the concentrated liquid was dried under reduced pressure to obtain an oily reaction product. This product was dissolved in ethyl acetate having a water content shown in Table 3 or water to prepare a solution having a concentration of about 13% by weight, and the solution was warmed to 30° C. and stirred for 6 hours. The amount produced of the diketopiperazine derivative (3) was analyzed with HPLC, and the relation between water content and the average increase in the diketopiperazine derivative (3) per hour was investigated. The results are shown in Table 3. The molar ratio in Table 3 means mol number of water per 1 mol of N-(1(S)-ethoxycarbonyl-3-phenylpropyl)-L-alanyl-L-proline.

TABLE 3

| Water content | | Average increase per hour |
|---|---|---|
| (% by weight) | (molar ratio) | (% by weight/hr) |
| 0.1 | 0.1 | 2.85 |
| 0.4 | 0.6 | 2.06 |
| 1.1 | 1.6 | 1.32 |
| 2.1 | 3.1 | 0.99 |
| 3.8 | 6.1 | 0.48 |
| 5.1 | 8.2 | 0.39 |
| 100 | 160 | 0.02 |

EXAMPLE 9

According to Example 1, N-(1(S)-ethoxycarbonyl-3-phenylpropyl)-L-alanyl-L-proline maleate was prepared. Thereto was added ethyl acetate containing 0.1% water or $H_2O$ to prepare a solution having a concentration of 16% by weight, and the solution was warmed to 60° C. and stirred for 6 hours. The amount produced of the diketopiperazine derivative (3) was analyzed with HPLC, and the relation between water content and the average increase in the diketopiperazine derivative (3) per hour was investigated. The results are shown in Table 4.

TABLE 4

| Solvents | Average increase per hour (% by weight/hr) |
|---|---|
| Ethyl acetate containing 0.1% water | 0.55 |
| $H_2O$ | 0.06 |

EXAMPLE 10

To 5.00 g (28.2 mmol) of 1,2,3,4-tetrahydroisoquinoline-3-carboxylic acid were added 20 ml of ethyl acetate and 10 ml of $H_2O$ and, then, the pH was adjusted to 10.5 with 30% by weight NaOH aqueous solution. The inner temperature was regulated to 20° C. and, then, 4.31 g (14.1 mmol) of a crystal of N-(1(S)-ethoxycarbonyl-3-phenylpropyl)-L-alanine. N-carboxyanhydride was slowly added over 5 hours with stirring. During the addition, the reaction mixture was maintained at a pH of 10.5±1.0 with adding dropwise 30% by weight NaOH aqueous solution, and simultaneously, the inner temperature was maintained at 20° C. and the agitating power was maintained at 1.3 kW/m³. After completion of the addition, the stirring was continued for 2 hour under the same conditions. The mixture was cooled to 5° C., and the pH thereof was adjusted to 4.5±0.2 with 35% by weight HCl. Then, under the same conditions, the stirring was continued for 10 minutes to complete the decarboxylation. The deposited material was removed by filtration under reduced pressure, and the organic phase was separated at 5° C. and the water phase was further extracted once with 20 ml of ethyl acetate at 10° C. . The resulting organic phases were mixed and then washed three times with $H_2O$ in an amount of 5% by volume of the organic phase at 5° C. The organic phase was concentrated under reduced pressure to obtain 6.43 g of an oil. The oil was dissolved in ethyl acetate having a water content shown in Table 5 to prepare a solution having a concentration of about 12% by weight, and the resulting solution was stirred for 6 hours at 10° C. The amount produced of the diketopiperazine derivative (3) was analyzed with HPLC, and the relation between water content and the average increase in the diketopiperazine derivative (3) per hour was investigated. The results are shown in Table 5.

TABLE 5

| Water content (% by weight) | Average increase per hour (% by weight/hr) |
|---|---|
| 0.1 | 5.3 |
| 1.0 | 2.2 |
| 2.1 | 1.7 |
| 3.8 | 1.3 |

EXAMPLE 11

According to Example 1, an ethyl acetate solution of N-(1(S)-ethoxycarbonyl-3-phenylpropyl)-L-alanyl-L-proline was prepared. To 50 ml of the ethyl acetate solution was added $H_2O$ in an amount of 10% by volume (based on ethyl acetate). The mixture was stirred for 10 minutes at each temperature shown in Table 6, and allowed to stand still for 10 minutes and, then, separated. The amount of N-(1(S)-ethoxycarbonyl-3-phenylpropyl)-L-alanyl-L-proline in the water-saturated organic phase was analyzed with HPLC, and the relation between the temperature and the partition ratio to the organic phase was investigated. The results are shown in Table 6.

TABLE 6

| Temperature (° C.) | Partition ratio to organic phase (%) |
|---|---|
| 5 | 26 |
| 10 | 35 |
| 20 | 57 |
| 25 | 72 |
| 30 | 88 |
| 40 | 94 |

EXAMPLE 12

To 22.02 g (191 mmol) of L-proline were added 20 ml of ethyl acetate and 22 ml of $H_2O$ and, then, the pH was adjusted to 10.5 with 30% by weight NaOH aqueous solution. The inner temperature was regulated to 19 to 20° C. and, then, thereto was slowly added dropwise a solution containing 29–20 g (96 mmol) of N-phenylpropyl )-L-alanine. N-carboxyanhydrine in 156 ml of ethyl acetate over 4 hours with stirring. During the dropping, the reaction mixture was maintained at a pH of 10.5±1.0 with adding dropwise 30% by weight NaOH aqueous solution, and simultaneously, the inner temperature was maintained at 19 to 20° C. and the agitating power was maintained at 0.7 kW/m³. After completion of the dropping, the stirring was continued for 1 hour under the same conditions. The inner temperature was raised to 30° C., and the pH thereof was adjusted to 4.5±0.2 with 35% by weight HCl. Under the same conditions, the stirring was continued for 10 minutes to complete the decarboxylation. The organic phase was separated at 30° C. and, then, the water phase was extracted once with 20 ml of ethyl acetate at 30° C. The resulting organic phases were mixed and cooled down to 0 to 3° C. and, then, back-extracted with 250 ml of $H_2O$. The reaction ratio was 98% and the extraction recovery was 94%. The amounts produced of the by-products were as follows: diketopiperazine derivative (3) 0.3% by weight, carboxy derivative (4) 0.6% by weight, N-(1(S)-ethoxycarbonyl-3-phenylpropyl)-L-alanine (5) 0.4% by weight.

The obtained 12% by weight aqueous solution of N-(1(S)-ethoxycarbonyl-3-phenylpropyl)-L-alanyl-L-proline was warmed to an inner temperature of 30° C. and thereto was added 10.73 g (93 mmol) of maleic acid with stirring. The stirring was continued for 1 hour under the same conditions and, then, the inner temperature was cooled down to 5° C. over 3 hours. To the mixture was added 62.05 g of NaCl and the stirring was continued for further 2 hours. The deposited crystal was taken out by filtration under reduced pressure, and quickly washed three times with 80 ml of $H_2O$ cooled to 0 to 3° C. The resulting wet crystal was dried under reduced pressure (20 to 50° C., 30→1 mmHg) to obtain 40.35 g (82 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 86%.

EXAMPLE 13

To 22.02 g (191 mmol) of L-proline were added 20 ml of ethyl acetate and 22 ml of $H_2O$ and, then, the pH was adjusted to 10.5 with 30% by weight NaOH aqueous solution. The inner temperature was regulated to 19 to 20° C. and, then, thereto was slowly added dropwise a solution containing 29.20 g (96 mmol) of N-(1(S)-ethoxycarbonyl-3-phenylpropyl)-L-alanine. N-carboxyanhydride in 156 ml of ethyl acetate over 4 hours with stirring. During the dropping, the reaction mixture was maintained at a pH of 10.5±0.5 with adding dropwise 30% by weight NaOH aqueous solution, and simultaneously, the inner temperature was maintained at 19 to 20° C. and the agitating power was maintained at 0.5 kW/m$^3$. After completion of the dropping, the stirring was continued for 1 hour under the same conditions. The inner temperature was raised to 30° C., and the pH thereof was adjusted to 4.5±0.2 with 35% by weight HCl. Under the same conditions, the stirring was continued for 10 minutes to complete the decarboxylation. The reaction ratio were 98% and the amounts produced of the by-products were as follows: diketopiperazine derivative (3) 0.5% by weight, carboxy derivative (4) 0.4% by weight, N-(1(S)-ethoxycarbonyl-3-phenylpropyl)-L-alanine (5) 0.6% by weight.

This two-phase liquid was stirred at an inner temperature of 30° C. and thereto was added 10.88 g (94 mmol) of maleic acid. The stirring was continued for 1 hour under the same conditions and, then, the inner temperature was cooled down to 5° C. over 3 hours, and the stirring was continued for further 2 hours. The deposited crystal was taken out by filtration under reduced pressure, and washed once with 80 ml of $H_2O$ cooled to 0 to 30° C. and once with 80 ml of ethyl acetate cooled to 5° C. The resulting wet crystal was dried under reduced pressure (20 to 50° C., 30→1 mmHg) to obtain 41.54 g (84 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 86%.

EXAMPLE 14

To 22.02 g (191 mmol) of L-proline were added 20 ml of methylene chloride and 22 ml of $H_2O$ and, then, the pH was adjusted to 10.5 with 30% by weight NaOH aqueous solution. The inner temperature was regulated to 19 to 20° C. and, then, thereto was slowly added dropwise a solution prepared by dissolving 29.20 g (96 mmol) of N-(1(S)-ethoxycarbonyl-3-phenylpropyl)-L-alanine. N-carboxyanhydride in 156 ml of methylene chloride, over 4 hours with stirring. During the dropping, the reaction mixture was maintained at a pH of 10.5±1.0 with adding dropwise 30% by weight NaOH aqueous solution, and simultaneously, the inner temperature was maintained at 19 to 20° C. and the agitating power was maintained at 1 kW/m$^3$. After completion of the dropping, the stirring was continued for 1 hour under the same conditions. The inner temperature was raised to 30° C., and the pH thereof was adjusted to 4.5±0.2 with 35% by weight HCl. Under the same conditions, the stirring was continued for 10 minutes to complete the decarboxylation. The organic phase was separated at 25° C. and, then, the water phase was extracted once with 20 ml of methylene chloride at 25° C. The resulting organic phases were mixed and then washed once with $H_2O$ in an amount of 5% by volume of the organic phase at 25° C. The water-saturated organic phase was analyzed with HPLC and, as a result, a solution containing 10% by weight N-(1(S)-ethoxycarbonyl-3-phenylpropyl)-L-alanyl-L-proline was obtained. The reaction ratio was 97% and the extraction recovery was 99% The amounts produced of the by-products were as follows: diketopiperazine derivative (3) 0.6% by weight, carboxy derivative (4) 0.5% by weight, N-(1(S)-ethoxycarbonyl-3-phenylpropyl)-L-alanine (5) 0.5% by weight.

Further, to this solution was added 10.87 g (94 mmol) of maleic acid with stirring at an inner temperature of 30° C. The stirring was continued for 1 hour under the same conditions and, then, the inner temperature was cooled down to 5° C. over 3 hours, and the stirring was continued for further 2 hours. The deposited crystal was taken out by filtration under reduced pressure, and washed once with 80 ml of methylene chloride cooled to 5° C. The resulting wet crystal was dried under reduced pressure (20 to 50° C., 30→1 mmHg) to obtain 43.41 g (88 mmol) of N-(1(S)-ethoxycarbonyl-3-phenylpropyl)-L-alanyl-L-proline maleate. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 92%.

EXAMPLE 15

According to Example 2, using 30% KOH aqueous solution instead of 30% NaOH aqueous solution, N-(1(S)-ethoxycarbonyl-3-phenylpropyl)-L-alanyl-L-proline was obtained. The reaction ratio was 96% and the amounts produced of the by-products were as follows: diketopiperazine derivative (3) at most 0.05% by weight, the carboxy derivative (4) 0.4% by weight and N-(1(S)-ethoxycarbonyl-3-phenylpropyl)-L-alanine (5) 0.6% by weight.

Further, according to Example 2, using the increased amount of maleic acid to 13.85 g (119 mmol) from 10.66 g (92 mmol), N-(1(S)-ethoxycarbonyl-3-phenylpropyl)-L-alanyl-L-proline maleate was obtained. The purity was at least 99% and the contents of the diketopiperazine derivative (3), carboxy derivative (4) and N-(1(S)-ethoxycarbonyl-3-phenylpropyl)-L-alanine (5) were respectively at most 0.05% by weight. The yield from N-(1(S)-ethoxycarbonyl-3-phenylpropyl)-L-alanine. N-carboxyanhydride was 90%.

EXAMPLE 16

According to Example 12 except for omitting the addition of NaCl, N-(1(S)-ethoxycarbonyl-3-phenylpropyl)-L-alanyl-L-proline maleate was obtained. The salting-out effect of NaCl was examined as compared with in Example 12. The results are shown in Table 7. The crystallization yield in Table 7 means a proportion of the crystallized maleate based on N-(1(S)-ethoxycarbonyl-3-phenylpropyl)-L-alanyl-L-proline, calculated by mole.

TABLE 7

| Solvents | Crystallization yield (%) |
| --- | --- |
| Aqueous solution | 83 |
| Aqueous solution + NaCl (Example 12) | 93 |

EXAMPLE 17

To 20.0 g (40.6 mmol) of N-(1(S)-ethoxycarbonyl-3-phenylpropyl)-L-alanyl-L-proline maleate containing 3.0% by weight N-(1(S)-ethoxycarbonyl-3-phenylpropyl)-L-alanine (5) was added 300 ml of $H_2O$ and, then, this mixture was heated to 60° C. to be dissolved. The mixture was cooled to 5° C. over 4 hours with stirring, and thereto was added 38 g of NaCl and the stirring was continued for further 1 hour. The deposited material was taken out by filtration and washed twice with 100 ml of $H_2O$ cooled to 0 to 3° C. The resulting crystal had a good filterability and a glossy and excellent crystal form. The resulting wet crystal was dried under reduced pressure (20 to 50° C., 30→1 mmHg) to obtain 17.2 g (34.9 mmol) of N-(1(S)-ethoxycarbonyl-3-phenylpropyl)-L-alanyl-L-proline maleate. The purity was at least 99% and the content of the N-(1(S)-ethoxycarbonyl-3-phenylpropyl)-L-alanine (5) was at most 0.05% by weight. During the operation, the production of the by-product diketopiperazine derivative (3) was not recognized.

EXAMPLE 18

To 20.0 g (40.6 mmol) of N-(1(S)-ethoxycarbonyl-3-phenylpropyl)-L-alanyl-L-proline maleate containing 3.0% by weight N-(1(S)-ethoxycarbonyl-3-phenylpropyl)-L-alanine (5) was added 300 ml of $H_2O$ and, then, this mixture was warmed to 30° C. The mixture was cooled to 5° C. over 4 hours with stirring, and thereto was added 38 g of NaCl and the stirring was continued for further 1 hour. The deposited material was taken out by filtration and washed twice with 100 ml of $H_2O$ cooled to 0 to 3° C. The resulting wet crystal was dried under reduced pressure (20 to 50° C., 30→1 mmHg) to obtain 17.2 g (34.9 mmol) of N-(i(S)-ethoxycarbonyl-3-phenylpropyl)-L-alanyl-L-proline maleate. The purity was at least 99% and the content of the N-(1(S)-ethoxycarbonyl-3-phenylpropyl)-L-alanine (5) was at most 0.05% by weight. During the operation, the production of the by-product diketopiperazine derivative (3) was not recognized.

EXAMPLE 19

To 20.0 g (40.6 mmol) of N-(1(S)-ethoxycarbonyl-3-phenylpropyl)-L-alanyl-L-proline maleate containing 3.0% by weight N-(1(S)-ethoxycarbonyl-3-phenylpropyl)-L-alanine (5) was added 300 ml of $H_2O$ and, then, this mixture was kept at 5° C. for 4 hours with stirring. Thereto was added 38 g of NaCl and the stirring was continued for further 1 hour. The deposited material was taken out by filtration and washed twice with 100 ml of $H_2O$ cooled to 0 to 3° C. The resulting wet crystal was dried under reduced pressure (20 to 50° C., 30→1 mmHg) to obtain 17.2 g (34.9 mmol) of N-(1(S)-ethoxycarbonyl-3-phenylpropyl)-L-alanyl-L-proline maleate. The purity was at least 99% and the content of the N-(1(S)-ethoxycarbonyl-3-phenylpropyl)-L-alanine (5) was at most 0.05% by weight. During the operation, the production of the by-product diketopiperazine derivative (3) was not recognized.

COMPARATIVE EXAMPLE 1

To 10.0 g (27.9 mmol) of a diketopiperazine derivative (6) of N-(1(S)-ethoxycarbonyl-3-phenylpropyl)-L-alanyl-L-proline were added 50 ml of ethyl acetate and 50 ml of $H_2O$, and the mixture was stirred at 60° C. for 8 hours. The production of N-(1(S)-ethoxycarbonyl-3-phenylpropyl)-L-alanyl-L-proline was not recognized.

INDUSTRIAL APPLICABILITY

According to the present invention, an N-(1(S)-ethoxycarbonyl-3-phenylpropyl)-L-alanyl-amino acid and a pharmacologically acceptable salt thereof having high quality can be simply and advantageously prepared with high yield and economical efficiency.

Concretely, N-(1(S)-ethoxycarbonyl-3-phenylpropyl)-L-alanyl-amino acid (2) can be obtained with high yield because the production of the by-product diketopiperazine derivative (3) is suppressed by carrying out, in an aqueous liquid, a series of operations of from production of the compound (2) to formation of a pharmacologically acceptable salt thereof and, if necessary, isolation of the salt. The present invention does not require to replace a solvent because the above-mentioned series of operations can be carried out in the same solvent and, therefore, the operation can simply be carried out.

Further, there can be obtained the compound (2) having a low content of a carboxy derivative (4) and N-(1(S)-ethoxycarbonyl-3-phenylpropyl)-L-alanine (5) as well as a diketopiperazine derivative (3), by carrying out the reaction for producing the compound (2) under a specific condition.

Additionally, N-(1(S)-ethoxycarbonyl-3-phenylpropyl)-L-alanyl-L-proline can be efficiently separated by carrying out extraction and separation operations under the specific temperature condition.

What is claimed is:

1. A process for preparing N-(1(S)-ethoxycarbonyl-3-phenylpropyl)-L-alanyl-L-proline which comprises producing N-(1(S)-ethoxycarbonyl-3-phenylpropyl)-L-alanyl-L-proline from L-proline and N-(1(S)-ethoxycarbonyl-3-phenylpropyl)-L-alanine. N-carboxyanhydride, wherein condensation is carried out by gradually adding at least one of N-(1(S)-ethoxycarbonyl-3-phenylpropyl)-L-alanine. N-carboxyanhydride and a basic pH adjusting agent to an aqueous liquid containing L-proline and, if necessary, N-(1(S)-ethoxycarbonyl-3-phenylpropyl)-L-alanine. N-carboxyanhydride, with the pH of the aqueous liquid maintained within a range of from 9 to 12, and then decarboxylation is carried out under between neutral and acidic condition to obtain N-(1(S)-ethoxycarbonyl-3-phenylpropyl)-L-alanyl-L-proline having a low content of a diketopiperazine derivative represented by a formula (6):

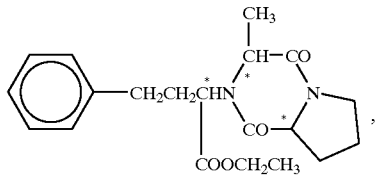

(6)

wherein all asymmetric carbon atoms with * have (S)-configuration, N-(1(S)-carboxy-3-phenylpropyl)-L-alanyl-L-proline represented by a formula (7):

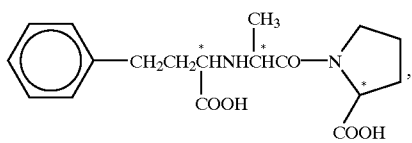

(7)

wherein all asymmertric carbon atoms with * have (S)-configuration, and N-(1(S)-ethoxycarbonyl-3-phenylpropyl)-L-alanine represented by a formula (5):

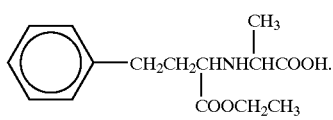

(5)

2. The process of claim 1 wherein at least one of the N-(1(S)-ethoxycarbonyl-3-phenylpropyl)-L-alanine. N-carboxyanhydride and the basic pH adjusting agent is added over at least ¼ hour.

3. The process of claim 1 or 2, wherein at least 2 molar equivalents of L-proline is used based on N-(1(S)-ethoxycarbonyl-3-phenylpropyl)-L-alanine. N-carboxyanhydride.

4. A process for preparing N-(1(S)-ethoxycarbonyl-3-phenylpropyl)-L-alanyl-L-proline which comprises producing N-(1(S)-ethoxycarbonyl-3-phenylpropyl)-L-alanyl-L-proline from L-proline and N-(1(S)-ethoxycarbonyl-3-phenylpropyl)-L-alanine. N-carboxyanhydride, wherein a reaction is started by adding N-(1(S)-ethoxycarbonyl-3-phenylpropyl)-L-alanine. N-carboxyanhydride to an aqueous liquid containing at least 2 molar equivalents of L-proline constituting a basic salt based on N-(1(S)-ethoxycarbonyl-3-phenylpropyl)-L-alanine. N-carboxyanhydride, and after the pH of the aqueous liquid reaches a range of from 9 to 12 a basic pH adjusting agent is gradually added to the aqueous liquid to carry out a condensation with the pH maintained within a range of from 9 to 12, and then decarboxylation is carried out under between neutral and acidic condition to obtain N-(1(S)-ethoxycarbonyl-3-phenylpropyl)-L-alanyl-L-proline having a low content of a diketopiperazine derivative represented by a formula (6):

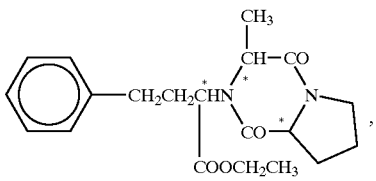

(6)

wherein all asymmetric carbon atoms with * have (S)-configuration, N-(1(S)-carboxy-3-phenylpropyl)-L-alanyl-L-proline represented by a formula (7):

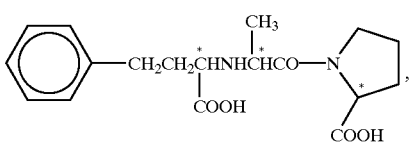

(7)

wherein all asymmetric carbon atoms with * have (S)-configuration, and N-(1(S)-ethoxycarbonyl-3-phenylpropyl)-L-alanyl-L-proline represented by a formula (5):

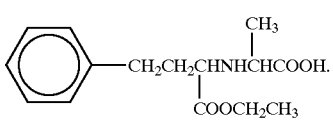

(5)

5. The process of claim 1, 2 or 4 wherein the aqueous liquid comprises an organic solvent and water in a weight ratio of from 96:4 to 0:100.

6. The process of claim 1, 2, or 4 wherein, in the reaction of L-proline and N-(1(S)-ethoxycarbonyl-3-phenylpropyl)-L-alanine. N-carboxyanhydride, stirring and mixing are carried out at an agitating power of at least 0.1 kW/m³.

7. The process of claim 5 wherein the organic solvent is at least one member selected from the group consisting of a halogenated hydrocarbon, a fatty acid ester, a ketone and an ether.

8. The process of claim 1, 2 or 4 wherein the reaction of producing N-(1(S)-ethoxy-carbonyl-3-phenylpropyl)-L-alanyl-L-proline is carried out in an aqueous liquid essentially consisting of water.

* * * * *